United States Patent
Nazare et al.

(10) Patent No.: US 9,221,784 B2
(45) Date of Patent: Dec. 29, 2015

(54) BENZO[1,3]DIOXINE DERIVATIVES AND THEIR USE AS LPAR5 ANTAGONISTS

(71) Applicant: SANOFI, Paris (FR)

(72) Inventors: Marc Nazare, Frankfurt am Main (DE); Detlef Kozian, Frankfurt am Main (DE); Martin Bossart, Frankfurt am Main (DE); Werngard Czechtizky, Frankfurt am Main (DE); Andreas Evers, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/401,041

(22) PCT Filed: May 16, 2013

(86) PCT No.: PCT/EP2013/060172
§ 371 (c)(1),
(2) Date: Nov. 13, 2014

(87) PCT Pub. No.: WO2013/171318
PCT Pub. Date: Nov. 21, 2013

(65) Prior Publication Data
US 2015/0111889 A1   Apr. 23, 2015

(30) Foreign Application Priority Data
May 18, 2012   (EP) .................................... 12305553

(51) Int. Cl.
| | | |
|---|---|---|
| *C07D 319/08* | (2006.01) | |
| *C07D 405/12* | (2006.01) | |
| *C07D 405/04* | (2006.01) | |
| *C07D 413/04* | (2006.01) | |
| *A61K 31/41* | (2006.01) | |
| *A61K 31/357* | (2006.01) | |
| *A61K 31/4245* | (2006.01) | |
| *C07D 403/12* | (2006.01) | |
| *C07D 401/04* | (2006.01) | |
| *C07D 401/12* | (2006.01) | |
| *C07D 403/04* | (2006.01) | |

(52) U.S. Cl.
CPC ............ *C07D 319/08* (2013.01); *C07D 401/04* (2013.01); *C07D 401/12* (2013.01); *C07D 403/04* (2013.01); *C07D 403/12* (2013.01); *C07D 405/04* (2013.01); *C07D 405/12* (2013.01); *C07D 413/04* (2013.01)

(58) Field of Classification Search
CPC .. C07D 319/08; C07D 405/12; C07D 405/04; C07D 401/04; C07D 403/12; C07D 401/12; C07D 403/04; C07D 413/04
See application file for complete search history.

(56) References Cited

U.S. PATENT DOCUMENTS 4,056,450 A     11/1977   McCauslan et al.

FOREIGN PATENT DOCUMENTS

| GB | 2022579 A | 12/1979 | |
| JP | 54144382 A | * 11/1979 | |
| WO | 2005000284 A2 | 1/2005 | |

OTHER PUBLICATIONS

Humbert, D.,"Synthesis of [4H] benzodioxine—1,3-carboxylic-2 acids and esters and study of their lipid-lowering activity", Eur J. Med (1983) 18:67-78.*
International Search Report for International Patent Application No. PCT/EP2013/060172 dated Jul. 16, 2013 (mailed Jul. 23, 2013) p. 1-10.
A. F. Littke et al., "Palladium-Catalyzed Coupling Reactions of Aryl Chlorides" Angew. Chem. Int. Ed. 2002, 41, 4176-4211.
A. Tunoori et al,, "Polymer-Bound Triphenylphosphine as Traceless Reagent for Mitsunobu Reactions in Combinatorial Chemistry: Synthesis of Aryl Ethers from Phenols and Alcohols" Tetrahedron Lett. 39 (1998) 8751-8754.
(Continued)

*Primary Examiner* — Samantha Shterengarts
*Assistant Examiner* — Matt Mauro
(74) *Attorney, Agent, or Firm* — McDonnell Boehnen Hulbert & Berghoff LLP

(57) ABSTRACT

The present invention relates to compounds of the formula (I), wherein the residues A, $R^1$ to $R^5$, $Z^1$ and $Z^2$ have the meanings indicated in the claims. The compounds of the formula (I) are valuable pharmacologically active compounds for use in the treatment of diverse disorders, for example cardiovascular disorders like thromboembolic diseases or restenoses. The compounds of the invention are effective antagonists of the platelet LPA receptor LPAR5 (GPR92) and can in general be applied in conditions in which an undesired activation of the platelet LPA receptor LPAR5, the mast cell LPA receptor LPAR5 or the microglia cell LPA receptor LPAR5 is present or for the cure or prevention of which an inhibition of the platelet, mast cell or microglia cell LPA receptor LPAR5 is intended. The invention furthermore relates to processes for the preparation of compounds of the formula (I), their use, in particular as active ingredients in medicaments, and pharmaceutical compositions comprising them.

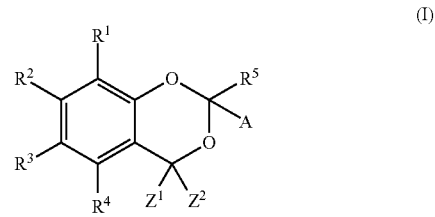

10 Claims, No Drawings

(56) References Cited

OTHER PUBLICATIONS

Amisten et al., "Gene expression profiling for the identification of G-protein coupled receptors in human platelets" Thromb Res (2008), 122, 47-57 (Oct. 24, 2007).

B. Yang et al. "Palladium-catalyzed amination of aryl halides and sulfonates" J. Organornet. Chem. 1999, 576, 125-146.

Blechert et al., "Total Synthesis of (±)-cis-Trikentrin A" Tetrahedron 1995, 51, 1167-1176.

Choi et al., "LPA Receprs Subypes and Biological Actions" Ann Rev Phamacol Toxicol (2010), 50, 157-186 (Oct. 21, 2009).

D. Chan et al., "New N- and O-Arylations with Phenylboronic Acids and Cupric Acetate" Tetrahedron Lett. 1998, 39, 2933-2936.

D. Crich et al., "Some Observations on the Mechanism of the Mitsunobu Reaction" J. Org. Chem. 54 (1989) 257-259.

D. J. Camp et al., "Mechanism of the Mitsunobu Esterification Reaction. 1. The Involvement of Phosphoranes and Oxyphosphonium Salts" J. Org. Chem, 54 (1989) 3045-3049.

D. Nichols et al., "1-(2,5-Dimethoxy-4-(trifluoromethyl)phenyl)-2-aminopropane: A Potent Serotonin 5-H T2A/2C Agonist" J. Med. Chem, 1994, 37, 4346-4351.

D.L. Hughes et al. "A Mechanistic Study of the Mitsunobu Esterification Reaction" J. Am. Chem. Soc. 110, 1988, 6487-6491.

F. Qing et al. "First synthesis of ortho-trifluoromethylated aryl triflates" J. Chem. Soc. Perkin Trans. I 1997, 3053-3057.

Fleicher et al., "Improved oral drug delivery: solubility limitations of prodrugs" Advanced Drug Delivery Reviews 19 (1996) 115-130.

Gilmer et al, "Synthesis, hydrolysis kinetics and anti-platelet effects of isosorbide mononitrate derivatives of aspirin" European J. Pharmaceutical Sciences, vol. 14, 3, 2001, p. 221-227.

J. Pelletier et al., "Mitsunobu reaction modifications allowing product isolation without chromatography: application to a small parallel library" Tetrahedron Lett. 41 (2000) 797-800.

J. Talley et al., "Reaction of Lithium o-Lithiophenoxide with Carbonyl Compounds" J. Org. Chem. 1984, 49, 5267-5269.

Kauch M et al., "Synthesis of Halogenated Phenols by Directed ortho-Lithiation and ipso-Iododesilylation Reacions of O-Aryl N-Isopropylcarbamates" Synthesis (2006), 1578-1589.

Khandoga et al, "The Plaque Lipid Lysophosphatidic Acid Stimulates Platelets Not Through the LPA1, LPA2 and LPA3 Receptor" J Thromb Haemost (2007), 5 Supplement 2, P-M-246, pp. 1-2.

Khandoga et al., "Lysphosphatidic acid-induced platelet shape change revealed through LPA1-5 receptor-selective probes and albumin" Platelets (2008), 19, 415-427.

Kinlcoh et al., "New targets for neuropathic pain therapeutics" Expert Opin Ther Targets (2005), 9, 685-698.

Lundequist, "Synergistic Induction of IL-23 Expression in Fibroblast-like Synoviocytes by IL-17 and TNF-Alpha: A Positive Feedback Loop in Rheumatoid Arthritis" J Allergy Clin Immunol (2008), 121, Suppl 1, Abstr 518, p. 1.

Morton J. G. M. et al., "Thieme Chemistry Jounal Awardees—Where are They Now? Efforts towards the Total Synthesis of Vinigrol" Synlett 2009, 23-27.

Muci R et al., "Practical Palladium Catalysts for C-N and C-O Bond Formation" Topics in current Chemistry 2002, 219, 131-209.

Netherton M.R. et al, "Palladium-Catalyzed Cross-Coupling Reactions of Unactivated Alkyl Electrophiles with Organometallic Compounds" Topics in Organometallic Chemistry 2005, 14 p. 85-108.

Noguchi et al., "Identificaton of p2y9/GPR23 as a Novel G Protein-coupled Receptor for Lysophosphatidic Acid, Structurally Distant from the Edg Family"J Biol Chem (2003), 278, 25600-25606.

Norrby K., "Mast cells and angiogenesis" APMIS, 2002, 110, 355-371.

O. Mitsunobu, "The Use of Diethyl Azodicarboxylate and Triphenylphosphine in Synthesis and Transformation of Natural Products" Synthesis, 1981, 1-28.

Oh et al., "Identificaton of Farnesyl Pyrophosphate and N-Arachidonylglycine as Endogenous Ligands for GPR92" J Biol Chem (2008), 283, 21054-21064.

P. Lam et al., "New Aryl/Heteroaryl C-N Bond Cross-coupling Reactions via Arylboronic Acid/Cupric Acetate Arylation" Tetrahedron Lett., 1998, 39, 2941-2944.

Q. Chen et al. "Methyl Chlorodifluoroacetate a Convenient Trifluoromethylating Agent" Tetrahedron Lett. 1991, 32, 7689-7690.

S. Buchwald et al., "A General and Efficient Copper Catalyst for the Amidation of Aryl Halides and the N-Arylation of Nitrogen Heterocycles" J. Am. Chem. Soc. 2001, 123, 7727-7729.

S. Buchwald et al., "Copper Catalyzed Coupling of Alkyanines and Ayrl Iodides: An Effcent Sysem Even in an Air Atmosphere" Organic Lett. 2002, 4, 581-584.

S. Kang et al. "Copper-catalyzed N-Arylation of Aryl Iodides with Benzamides or Nitrogen Heterocycles in the Presence of Ethylenediamine" Synlett 2002, 3, 427-430.

Simon et al., "Human Platelet Aggregation Induced by 1-Alkyl-Lysophosphatidic Acid and Its Analogs : A New Group of Phospholipid Mediators?" Biochem Biophys Res Commun (1982), 108, 1743-1750.

T. Fuchikami et al. "A Novel and Convenient Method for Trifluoromethylation of Organic Halides Using CF3SiR'3/KF/Cu(I) System" Tetrahedron Lett. 1991, 32, 91-94.

T. Sakamoto et al., "Palladium-catalyzed cyanation of aryl and heteroaryl iodides with copper(I) cyanide" J. Chem. Soc. Perkin Trans I, 1999, 2323-2326

Toews et al., "Lysophosphatidic acid in airway function and disease" Biochim Biophys Acta (2002), 1582, 240-250.

Tokumura et al., "Human platelets respond differentially to lysophosphatidic acids having a highly unsaturated fatty acyl group and alkyl ether-linked lysophosphatidic acids" Biochem J (2002), 365, 617-628.

Turner et al, "Origin of Enantiomeric Selectivity in the Aryloxyphenoxypropionic Acid Class of Herbicidal Acetyl Coenzyme A Carboxylase (ACCase) Inhibitors" J. Agric. Food Chem (2002), 50, 4554-4566.

Van Meeteren et al., "Autotaxin, a Secreted Lysophospholipase D, Is Essential for Blood Vessel Formation during Deveopment" Mol Cell Biol (2006), 26, 5015-5022.

Wang et al, "Novel Photolabile Protecting Group for Carbonyl Compounds" Org Lett, 2007, 9, 1533-1535.

Williams et al., "Lysophosphatidic Acid 2 Receptor-mediated Supramolecuiar ComplexFormation Regulates Its Antiapoptotic Effect" J Biol Chem (2009), 284, 14558-14571.

Yus et al., "New Homologation of 2-Hydroxy and 2-Mercapto Benzylic Aicohols" Tetrahedron 1997, 53, 17373-17382.

Zuo et al,, "Inflammation and hyperalgesia induced by nerve injury in the rat: a key role of mast cells" Pain (2003), 105, 467-479.

\* cited by examiner

BENZO[1,3]DIOXINE DERIVATIVES AND THEIR USE AS LPAR5 ANTAGONISTS

This application is a national stage application under 35 U.S.C. §371 of International Application No. PCT/EP2013/060172, filed May 16, 2013, which claims priority of European Application No. 12305553.5 filed on May 18, 2012, the disclosure of which is explicitly incorporated by reference herein.

The present invention relates to compounds of the formula I,

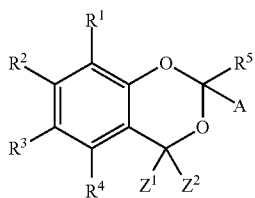

wherein the residues A, $R^1$ to $R^5$, $Z^1$ and $Z^2$ have the meanings indicated below. The compounds of the formula I are valuable pharmacologically active compounds for use in the treatment of diverse disorders. Compounds of the formula I exhibit a strong anti-aggregating effect on platelets and thus an anti-thrombotic effect and are suitable, for example, for the therapy and prophylaxis of cardiovascular disorders like thromboembolic diseases or restenoses. In addition, compounds of the formula I inhibit LPA-mediated activation of mast cells and microglia cells. The compounds of the invention are antagonists of the platelet LPA receptor LPAR5 (GPR92) and can in general be applied in conditions in which an undesired activation of the platelet LPA receptor LPAR5, the mast cell LPA receptor LPAR5 or the microglia cell LPA receptor LPAR5 is present, or for the cure or prevention of which an inhibition of the platelet, mast cell or microglia cell LPA receptor LPAR5 is intended. The invention furthermore relates to processes for the preparation of compounds of the formula I, their use, in particular as active ingredients in medicaments, and pharmaceutical compositions comprising them.

In the industrialized world thrombotic complications are one of the major causes of death. Examples of conditions associated with pathological thrombus formation include deep vein thrombosis, venous and arterial thromboembolism, thrombophlebitis, coronary and cerebral arterial thrombosis, cerebral embolism, renal embolism, pulmonary embolism, disseminated intravascular coagulation, transient ischemic attacks, strokes, acute myocardial infarction, peripheral vascular disease, preeclampsia/eclampsia, and thrombotic cytopenic purpura. Also during or following invasive procedures, including insertion of endovascular devices and protheses, carotid endarterectomy, angioplasty, CABG (coronary artery bypass graft) surgery, vascular graft surgery, and stent placements, thrombotic and restenotic complications could occur.

Platelet aggregation plays a critical role in these intravascular thrombotic events. Platelets can be activated by mediators released from circulating cells and damaged endothelial cells lining the vessel or by exposed subendothelial matrix molecules such as collagen, lysophosphatidic acid or by thrombin, which is formed in the coagulation cascade. Following activation, platelets, which normally circulate freely in the vasculature, and other cells, accumulate at the site of a vessel injury to form a thrombus and recruit more platelets to the developing thrombus. During this process, thrombi can grow to a sufficient size to partly or completely block arterial blood vessels. In veins thrombi can also form in areas of stasis or slow blood flow. These venous thrombi can create emboli that travel through the circulatory system, as they easily detach portions of themselves. These traveling emboli can block other vessels, such as pulmonary or coronary arteries, which can result in the above-mentioned pathological outcomes such as pulmonary or coronary embolism. In summary, for venous thrombi, morbidity and mortality arise primarily after embolization or distant blockade of vessels, whereas arterial thrombi cause serious pathological conditions by local blockade.

Lysophosphatidic acid (LPA) is an important bioactive phospholipid with a wide range of cellular functions. Levels of LPA are tightly regulated via its synthesis, controlled by two different pathways. The first consisting of phospholipase D (PLD) and phospholipase A2 ($PLA_2$) activity, the second consisting of $PLA_2$ and lysophospholipase D (lysoPLD) activity. The most commonly used LPA in laboratory praxis is 18:1 LPA (1-acyl-2-hydroxy-sn-glycero-3-phosphate). However, many other forms of LPA exist in the organism, with varying length of the fatty acid chain, different saturation grades and coupling of the fatty acid chain to the glycerol backbone, i.e. coupling via an ester or ether bond (Choi et al., Ann Rev Pharmacol Toxicol (2010), 50, 157-186). A key enzyme for LPA synthesis is autotaxin (ATX), Enpp2 in mice. It has been shown that ATX has lysoPLD activity and that $Enpp2^{-/-}$ mice die in utero at day 9.5. $Enpp2^{+/-}$ mice show reduced LPA plasma levels (van Meeteren et al., Mol Cell Biol (2006), 26, 5015-5022). LPA exerts its extracellular biological effects through binding to G protein-coupled receptors. So far, five different LPA receptors have been identified, LPAR1 (EDG2), LPAR2 (EDG4), LPAR3 (EDG7), LPAR4 (GPR23 and LPAR5 (GPR92). All described LPA receptors belong to the class A (Rhodopsin-like class) of G protein-coupled receptors (GPCRs).

LPAR5 has been identified in mouse and human dorsal root ganglia and reduced perception of pain was seen in $LPAR5^{-/-}$ mice (Oh et al., J Biol Chem (2008), 283, 21054-21064; Kinloch et al., Expert Opin Ther Targets (2005), 9, 685-698). The coupling of LPARs to different G protein subunits in different cell types in concert with the differential expression of the various LPA receptors on the same cell is the primary reason for the great variety of biological effects of LPA. The influence of LPA on the activation of human platelets has been described in the early 1980s. 1-O-alkyl-sn-glycero-3-phosphate (an alkyl-LPA) has been identified to be a more potent activator in platelets compared to oleoyl-LPA (Simon et al., Biochem Biophys Res Commun (1982), 108, 1743-1750). Further studies pointed out that the so-called alkyl-LPA receptor is neither an EDG-type LPA receptor nor GPR23 (Tokumura et al., Biochem J (2002), 365, 617-628; Noguchi et al., J Biol Chem (2003), 278, 25600-25606; Khandoga et al., J Thromb Haemost (2007), 5 Supplement 2: P-M-246 (ISTH 2007)). When transiently expressed in the rat hepatoma cell line RH7777, LPAR5 can be activated more strongly with alkyl-LPA than acyl-LPA (Williams et al., J Biol Chem (2009), 284, 14558-14571). These data were in line with the LPA-mediated activation observed for human blood platelets, in which the functional effect of alkyl-LPA, in terms of inducing platelet aggregation is more pronounced than the effect of acyl-LPA. In addition, the LPA-receptors LPAR4 and LPAR5 are highly expressed by human platelets (Amisten et al., Thromb Res (2008), 122, 47-57). In contrast to LPAR5, which is coupled to $G_q$, LPAR4 couples to $G_s$ and can therefore be excluded to participate in LPA-mediated activation of human platelets. Consequently, LPAR5 was discussed to be the central LPA-receptor responsible for LPA-mediated activation in human platelets (Khandoga et al., Platelets (2008), 19, 415-427). High expression of LPAR5 in human mast cell lines has been demonstrated, for example by Lundequist (Lundequist, J Allergy Clin Immunol (2008), 121, Suppl 1, Abstr 518), and further analyses.

Mast cells are part of the immune system and generated as precursor cells in the bone marrow, differentiating to mature mast cells in the homing tissue. Mast cells participate in a variety of pathophysiological processes that range from antimicrobial defense to anaphylaxis and inflammatory arthritis and have thus been discussed to be related to allergic responses. When activated, mast cells degranulate and release a plethora of mediators (cytokines such as TNFa, MCP-1, Rantes) into the interstitium. This indicates a direct contribution of mast cells to neuropathic pain by releasing algogenic mediators after degranulation.

Apart from the above discussed role of mast cells, the broad spectrum of mast cell functions explains why mast cells are involved in a variety of pathologies apart from allergic responses related to pathologies with an inflammatory component. These diseases comprise hyperalgesia, asthma, multiple sclerosis and angiogenesis to name only a few (Zuo et al., Pain (2003), 105, 467-479; Toews et al., Biochim Biophys Acta (2002), 1582, 240-250; Norby, APMIS (2002), 110, 355-371). Treatment of the human mast cell line LAD2 with a short hairpin RNA targeting LPAR5 down-regulates LPAR5 expression and attenuates MIP-1β following LPA activation (Lundequist, J Allergy Clin Immunol (2008), 121, Suppl 1, Abstr 518).

Analyses of the LPA receptor profile in the murine microglia cell line BV-2, confirmed a high expression of LPAR5 in microglia cells, which are like mast cells a cell population of the inflammatory system. The finding that LPAR5 is highly expressed not only in mast cells but as well in microglia cells underlines the central role of LPAR5 in the development and progression of inflammatory disorders, such as hyperalgesia, asthma, multiple sclerosis, angiogenesis and others.

Further experiments confirmed that in human platelets and in human mast cells and microglia cells LPAR5 is the key LPA-receptor responsible for LPA-mediated activation. In view of the relevance of LPAR5 for various disease states there is a need for compounds which efficiently inhibit LPAR5 and, for example, consequently inhibit mast cell activation or platelet activation in pathological settings, and allow novel therapeutic options for treating disorders. Thus, it is an object of the present invention to provide LPAR5 antagonists, which antagonize the effect of endogenous LPA on its LPAR5 receptor and which have further advantageous properties, for instance stability in plasma and liver and selectivity versus other receptors whose agonism or antagonism is not intended. This object is achieved in accordance with the invention by providing the benzo[1,3]dioxine derivatives of the formula I, which exhibit excellent LPAR5 antagonistic activity and are favorable agents with high bioavailability, and can be used for inhibiting platelet aggregation and treating thromboembolic diseases, for example.

In GB 2022579 and in D. Humbert et al., Eur. J. Med. Chem. (1983), 18, 67-78, certain 4H-benzo[1,3]dioxine-2-carboxylic acids and their alkyl esters are described, in which one of the groups corresponding to the groups $Z^1$ and $Z^2$ in the compounds of the formula I can among others be hydrogen, alkyl containing up to six carbon atoms or cyclohexyl, and the other of the said groups can among others be hydrogen, alkyl containing up to six carbon atoms, cyclohexyl or phenyl, wherein the phenyl group as well as the benzene moiety of the benzo[1,3]dioxine ring system are independently of each other unsubstituted or substituted by one substituent selected from the series consisting halogen, trifluoromethyl, cyclohexyl, $(C_1-C_3)$-alkyl-O—, $(C_1-C_3)$-alkyl and para-chlorophenoxy. Specifically disclosed compounds in which one of the groups corresponding to $Z^1$ and $Z^2$ is cyclohexyl, are 6-chloro-4-cyclohexyl-4-phenyl-4H-benzo[1,3]dioxine-2-carboxylic acid and its methyl ester and 6-chloro-4,4-dicyclohexyl-4H-benzo[1,3]dioxine-2-carboxylic acid. For some of the compounds described in GB 2022579 and D. Humbert et al., in which the groups corresponding to $Z^1$ and $Z^2$ are not cyclohexyl, data are given which show their hypotriglyceridaemic and hypocholesterolaemic activity and in view of which the compounds are regarded as useful for treatment of hyperlipaemia. An activity of the compounds on platelet aggregation is neither disclosed nor suggested in GB 2022579 and in D. Humbert et al. Other 4H-benzo[1,3]dioxine-2-carboxylic acids and derivatives thereof are described, for example, in J. A. Turner et al., J. Agric. Food Chem. (2002), 50, 4554-4566, which relates to herbicidal acetyl coenzyme A carboxylase inhibitors, or in U.S. Pat. No. 4,056,540, which relates to compounds having anticonvulsant and antiarrhythmic activity.

A subject of the present invention are the compounds of the formula I, in any of their stereoisomeric forms or a mixture of stereoisomeric forms in any ratio, and the pharmaceutically acceptable salts thereof,

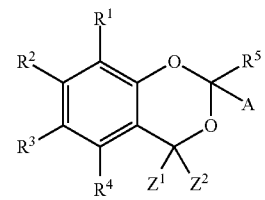

wherein

A is selected from the series consisting of $R^{11}$—O—C(O)—, $R^{12}$—N($R^{13}$)—C(O)— and $Het^1$;

$R^1$, $R^2$, $R^3$ and $R^4$ are independently of each other selected from the series consisting of hydrogen, halogen, $(C_1-C_4)$-alkyl, Ar—$(C_1-C_4)$-alkyl-, Ar, $Het^2$, $(C_1-C_4)$-alkyl-C(O)—, Ar—C(O)—, cyano, $R^{14}$—N($R^{15}$)—C(O)—, $Het^3$-C(O)—, hydroxy, $(C_1-C_4)$-alkyl-O—, Ar—O—, Ar—$(C_1-C_4)$-alkyl-O—, $(C_1-C_4)$-alkyl-S(O)$_n$—, Ar—S(O)$_n$—, $R^{11}$—N($R^{12}$)—S(O)$_2$—, $Het^3$-S(O)$_2$—, $(C_1-C_4)$-alkyl-NH—, di(($C_1-C_4$)-alkyl)N—, Ar—NH— and Ar—N(($C_1-C_4$)-alkyl), and either the groups $R^1$ and $R^2$, or the groups $R^2$ and $R^3$, or the groups $R^3$ and $R^4$, together with the carbon atoms carrying them, can form a carbocyclic ring which is selected from the series consisting of benzene and 5-membered to 7-membered cycloalkane, wherein the benzene ring is unsubstituted or substituted by one or more identical or different substituents selected from the series consisting of halogen, $(C_1-C_4)$-alkyl, cyano, $(C_1-C_4)$-alkyl-O— and $(C_1-C_4)$-alkyl-S(O)$_n$—, and the cycloalkane ring is unsubstituted or substituted by one or more identical or different substituents selected from the series consisting of fluorine and $(C_1-C_4)$-alkyl;

$R^5$ is selected from the series consisting of hydrogen and $(C_1-C_4)$-alkyl;

$R^{11}$, $R^{12}$, $R^{13}$, $R^{14}$ and $R^{15}$ are independently of each other selected from the series consisting of hydrogen and $(C_1-C_4)$-alkyl;

one of the groups $Z^1$ and $Z^2$ is $(C_3$-$C_8)$-cycloalkyl and the other is selected from the series consisting of hydrogen, $(C_1$-$C_8)$-alkyl, $(C_3$-$C_8)$-cycloalkyl and phenyl, wherein all cycloalkyl groups are independently of each other unsubstituted or substituted by one or more identical or different substituents selected from the series consisting of fluorine, $(C_1$-$C_4)$-alkyl and $(C_1$-$C_4)$-alkyl-O—, and the phenyl group is unsubstituted or substituted by one or more identical or different substituents selected from the series consisting of halogen, $(C_1$-$C_4)$-alkyl, cyano, $(C_1$-$C_4)$-alkyl-O— and $(C_1$-$C_4)$-alkyl-S(O)$_n$—;

Ar is phenyl or an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1$-$C_4)$-alkyl, cyano, $(C_1$-$C_4)$-alkyl-O— and $(C_1$-$C_4)$-alkyl-S(O)$_n$—;

Het$^1$ is a partially unsaturated or aromatic, 5-membered or 6-membered, monocyclic heterocycle which comprises one to four identical or different ring heteroatoms selected from the series consisting of N, O and S, which is bonded via a ring carbon atom, and which is unsubstituted or substituted by one or more identical or different substituents selected from the series consisting of $(C_1$-$C_4)$-alkyl, hydroxy and oxo;

Het$^2$ is a saturated, 4-membered to 7-membered, monocyclic heterocycle which comprises one or two identical or different ring heteroatoms selected from the series consisting of N, O and S, which is bonded via a ring carbon atom or a ring nitrogen atom, and which is unsubstituted or substituted by one or more identical or different substituents selected from the series consisting of fluorine and $(C_1$-$C_4)$-alkyl;

Het$^3$ is a saturated 4-membered to 7-membered, monocyclic heterocycle which comprises a ring nitrogen atom via which Het$^3$ is bonded, and zero or one further ring heteroatom selected from the series consisting of N, O and S, and which is unsubstituted or substituted by one or more identical or different substituents selected from the series consisting of fluorine and $(C_1$-$C_4)$-alkyl;

n is selected from the numbers 0, 1 and 2;

wherein all alkyl groups are unsubstituted or substituted by one or more fluorine substituents;

provided that the compound of the formula I is not 6-chloro-4-cyclohexyl-4-phenyl-4H-benzo[1,3]dioxine-2-carboxylic acid, 6-chloro-4-cyclohexyl-4-phenyl-4H-benzo[1,3]dioxine-2-carboxylic acid methyl ester or 6-chloro-4,4-dicyclohexyl-4H-benzo[1,3]dioxine-2-carboxylic acid.

In one embodiment, the present invention relates to compounds of the formula I, wherein A is selected from the series consisting of $R^{11}$—O—C(O)—, $R^{12}$—N($R^{13}$)—C(O)— and Het$^1$;

$R^1$, $R^2$, $R^3$ and $R^4$ are independently of each other selected from the series consisting of hydrogen, halogen, $(C_1$-$C_4)$-alkyl, Ar—$(C_1$-$C_4)$-alkyl-, Ar, Het$^2$, $(C_1$-$C_4)$-alkyl-C(O)—, Ar—C(O)—, $R^{14}$—N($R^{15}$)—C(O)—, Het$^3$-C(O)—, $(C_1$-$C_4)$-alkyl-O—, Ar—O—, Ar—$(C_1$-$C_4)$-alkyl-O—, $(C_1$-$C_4)$-alkyl-S(O)$_n$—, Ar—S(O)$_n$—, $R^{11}$—N($R^{12}$)—S(O)$_2$—, Het$^3$-S(O)$_2$—, $(C_1$-$C_4)$-alkyl-NH— and di(($C_1$-$C_4)$-alkyl)N—, and either $R^1$ and $R^2$, or $R^2$ and $R^3$, or $R^3$ and $R^4$, together with the carbon atoms carrying them, can form a carbocyclic ring which is selected from the series consisting of benzene and 5-membered or 6-membered cycloalkane, wherein the benzene ring is unsubstituted or substituted by one or more identical or different substituents selected from the series consisting of halogen and $(C_1$-$C_4)$-alkyl, and the cycloalkane ring is unsubstituted or substituted by one or more identical or different substituents selected from the series consisting of fluorine and $(C_1$-$C_4)$-alkyl;

$R^5$ is selected from the series consisting of hydrogen and $(C_1$-$C_4)$-alkyl;

$R^{11}$, $R^{12}$, $R^{13}$, $R^{14}$ and $R^{15}$ are independently of each other selected from the series consisting of hydrogen and $(C_1$-$C_4)$-alkyl;

one of the groups $Z^1$ and $Z^2$ is $(C_3$-$C_8)$-cycloalkyl and the other is selected from the series consisting of hydrogen, $(C_1$-$C_8)$-alkyl, $(C_3$-$C_8)$-cycloalkyl and phenyl, wherein all cycloalkyl groups are independently of each other unsubstituted or substituted by one or more identical or different substituents selected from the series consisting of fluorine, $(C_1$-$C_4)$-alkyl and $(C_1$-$C_4)$-alkyl-O—, and the phenyl group is unsubstituted or substituted by one or more identical or different substituents selected from the series consisting of halogen, $(C_1$-$C_4)$-alkyl, cyano, $(C_1$-$C_4)$-alkyl-O— and $(C_1$-$C_4)$-alkyl-S(O)$_n$—;

Ar is phenyl or an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1$-$C_4)$-alkyl, cyano, $(C_1$-$C_4)$-alkyl-O— and $(C_1$-$C_4)$-alkyl-S(O)$_n$—;

Het$^1$ is a partially unsaturated or aromatic, 5-membered monocyclic heterocycle which comprises one to four identical or different ring heteroatoms selected from the series consisting of N, O and S, which is bonded via a ring carbon atom, and which is unsubstituted or substituted by one or more identical or different substituents selected from the series consisting of $(C_1$-$C_4)$-alkyl, hydroxy and oxo;

Het$^2$ is a saturated, 4-membered to 7-membered, monocyclic heterocycle which comprises one or two identical or different ring heteroatoms selected from the series consisting of N, O and S, which is bonded via a ring carbon atom or a ring nitrogen atom, and which is unsubstituted or substituted by one or more identical or different substituents selected from the series consisting of fluorine and $(C_1$-$C_4)$-alkyl;

Het$^3$ is a saturated 4-membered to 7-membered, monocyclic heterocycle which comprises a ring nitrogen atom via which Het$^3$ is bonded, and zero or one further ring heteroatom selected from the series consisting of N, O and S, and which is unsubstituted or substituted by one or more identical or different substituents selected from the series consisting of fluorine and $(C_1$-$C_4)$-alkyl;

n is selected from the numbers 0, 1 and 2;

wherein all alkyl groups are unsubstituted or substituted by one or more fluorine substituents;

and all stereoisomeric forms thereof and mixtures of stereoisomeric forms in any ratio, and the pharmaceutically acceptable salts thereof.

In another embodiment the present invention relates to compounds of the formula I, wherein A is selected from $R^{11}$—O—C(O)— or Het$^1$;

$R^1$, $R^2$, $R^3$ and $R^4$ are independently of each other selected from the series consisting of hydrogen, halogen, $(C_1$-$C_4)$-alkyl, Ar—$(C_1$-$C_4)$-alkyl-, Ar, Het$^2$, $(C_1$-$C_4)$-alkyl-C(O)—, Ar—C(O)—, $R^{14}$—N($R^{15}$)—C(O)—, Het$^3$-C(O)—, $(C_1$-$C_4)$-alkyl-O—, Ar—O—, Ar—$(C_1$-$C_4)$-alkyl-O—, $R^{11}$—N($R^{12}$)—S(O)$_2$—, Het$^3$-S(O)$_2$—, $(C_1$-$C_4)$-alkyl-NH— and di(($C_1$-$C_4)$-alkyl)N—, and either the groups $R^1$ and $R^2$, or $R^2$ and $R^3$, or $R^3$ and $R^4$, together with the carbon atoms carrying them, can form a carbocyclic ring which is selected from the series consisting of benzene and 5-membered or 6-membered cycloalkane, wherein the benzene ring is unsubstituted or substituted by one or more identical or different substituents selected from the series consisting of halogen and $(C_1-C_4)$-alkyl, and the cycloalkane ring is unsubstituted or substituted by one or more identical or different substituents selected from the series consisting of fluorine and $(C_1-C_4)$-alkyl;

$R^5$ is selected from the series consisting of hydrogen and $(C_1-C_4)$-alkyl;

$R^{11}$, $R^{12}$, $R^{14}$ and $R^{15}$ are independently of each other selected from the series consisting of hydrogen and $(C_1-C_4)$-alkyl;

one of the groups $Z^1$ and $Z^2$ is $(C_3-C_8)$-cycloalkyl and the other is selected from the series consisting of hydrogen, $(C_1-C_4)$-alkyl, $(C_3-C_8)$-cycloalkyl and phenyl, wherein all cycloalkyl groups are independently of each other unsubstituted or substituted by one or more identical or different substituents selected from the series consisting of fluorine and $(C_1-C_4)$-alkyl, and the phenyl group is unsubstituted or substituted by one or more identical or different substituents selected from the series consisting of halogen and $(C_1-C_4)$-alkyl;

Ar is phenyl or an aromatic, 5-membered or 6-membered, monocyclic heterocycle which comprises one or two identical or different ring heteroatoms selected from the series consisting of N, O and S, which are all unsubstituted or substituted by one or more identical or different substituents selected from the series consisting of halogen, $(C_1-C_4)$-alkyl and $(C_1-C_4)$-alkyl-O—;

Het$^1$ is selected from the series consisting of

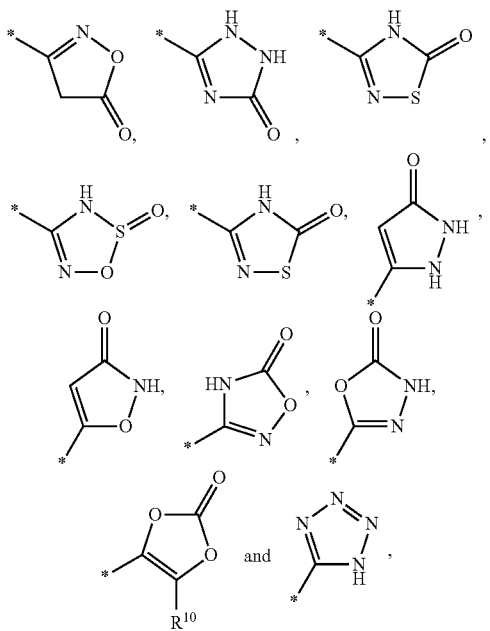

wherein $R^{10}$ is selected from the series consisting of hydrogen and $(C_1-C_4)$-alkyl;

Het$^2$ is a saturated, 5-membered or 6-membered, monocyclic heterocycle which comprises one or two identical or different ring heteroatoms selected from the series consisting of N, O and S, which is bonded via a ring carbon atom or a ring nitrogen atom, and which is unsubstituted or substituted by one or more identical or different substituents selected from the series consisting of fluorine and $(C_1-C_4)$-alkyl;

Het$^3$ is a saturated 5-membered or 6-membered, monocyclic heterocycle which comprises a ring nitrogen atom via which Het$^3$ is bonded, and zero or one further ring heteroatom selected from the series consisting of N, O and S, and which is unsubstituted or substituted by one or more identical or different substituents selected from the series consisting of fluorine and $(C_1-C_4)$-alkyl;

wherein all alkyl groups are unsubstituted or substituted by one or more fluorine substituents;

and all stereoisomeric forms thereof and mixtures of stereoisomeric forms in any ratio, and the pharmaceutically acceptable salts thereof.

In another embodiment the present invention relates to compounds of the formula I, wherein A is selected from the series consisting of $R^{11}$—O—C(O)—,

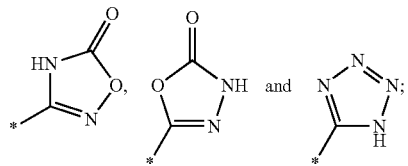

$R^1$, $R^2$, $R^3$ and $R^4$ are independently of each other selected from the series consisting of hydrogen, halogen, $(C_1-C_4)$-alkyl, $(C_1-C_4)$-perfluoroalkyl, $(C_1-C_4)$-alkyl-O—, $(C_1-C_4)$-perfluoroalkyl-O—, phenyl, pyrrolyl, pyridinyl, pyridinyl-O—, pyrrolidinyl-S(O)$_2$—, morpholinyl, Ar—C(O)—, Ar—O—, di((C$_1$-C$_4$)-alkyl)N—, Ar—(C$_1$-C$_4$)-alkyl- and Ar—(C$_1$-C$_4$)-alkyl-O—, and either the groups $R^1$ and $R^2$, or $R^2$ and $R^3$, or $R^3$ and $R^4$, together with the carbon atoms carrying them, can form a benzene ring or a cyclohexane ring, wherein the benzene ring is unsubstituted or substituted by one or more identical or different substituents selected from the series consisting of halogen and $(C_1-C_4)$-alkyl, and the cyclohexane ring is unsubstituted or substituted by one or more identical or different substituents selected from the series consisting of fluorine and $(C_1-C_4)$-alkyl;

$R^5$ is hydrogen or methyl;

$Z^1$ and $Z^2$ are identical and are $(C_3-C_8)$-cycloalkyl, or one of the residues $Z^1$ and $Z^2$ is $(C_3-C_8)$-cycloalkyl and the other is hydrogen or phenyl;

Ar is phenyl which is unsubstituted or substituted by one or two identical or different substituents selected from the series consisting of halogen and $(C_1-C_4)$-alkyl-O—;

and all stereoisomeric forms thereof and mixtures of stereoisomeric forms in any ratio, and the pharmaceutically acceptable salts thereof.

In one embodiment compounds of the formula I are defined as above and A is a residue selected from the series consisting of $R^{11}$—O—C(O)— and Het$^1$, in another embodiment A is $R^{11}$—O—C(O)—, and in another embodiment A is HO—C(O)—. In one embodiment, the group Het$^1$ representing A is any one or more of the groups

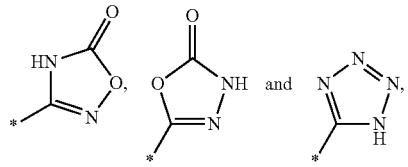

wherein in the formulae of these groups as well as in the formulae of other specific groups $Het^1$ representing A the line marked with an asterisk denotes the free bond via which the group is attached to the ring carbon atom carrying the group A.

In one embodiment, compounds of the formula I are defined as above and $R^1$, $R^2$, $R^3$ and $R^4$ are identical or different and independently of one another selected from the series consisting of any one or more of the groups hydrogen;

halogen;

$(C_1-C_4)$-alkyl, wherein in one embodiment $(C_1-C_4)$-alkyl is selected from any one or more of the groups methyl, ethyl, n-propyl, isopropyl, n-butyl, isobutyl, sec-butyl and t-butyl;

$C_1-C_4$)-alkyl-O—, wherein in one embodiment $(C_1-C_4)$-alkyl-O— is selected from any one or more of the groups methyl-O—, ethyl-O—, propyl-O— and butyl-O—; Ar, wherein in one embodiment Ar is selected from any one or more of the groups phenyl, pyrrolyl and pyridinyl;

Ar—C(O)—, wherein in one embodiment Ar—C(O)— is phenyl-C(O)—, and in one embodiment is unsubstituted or substituted, in another embodiment is substituted, for example by one or two halogen substituents, for example chlorine substituents, and in another embodiment Ar—C(O)— is a chloro-substituted benzoyl group, for example Cl-phenyl-C(O)—;

Ar—O—, wherein in one embodiment Ar—O— is selected from any one or more of the groups pyridinyl-O— and phenyl-O—, and in one embodiment is unsubstituted or substituted, in another embodiment is substituted, for example by one or two halogen substituents, for example chlorine substituents, and in another embodiment Ar—O— is selected from any one or more of the groups pyridinyl-O— and Cl-phenyl-O—; di(($C_1-C_4$)-alkyl)N—, wherein in one embodiment di(($C_1-C_4$)-alkyl)N— is selected from any one or more of the groups (methyl)$_2$N— and (ethyl)$_2$N—;

Ar—($C_1-C_4$)-alkyl-, wherein in one embodiment the group Ar in Ar—($C_1-C_4$)-alkyl- is phenyl and in another embodiment Ar—($C_1-C_4$)-alkyl- is benzyl, and in one embodiment Ar is unsubstituted or substituted, in another embodiment it is substituted, for example by one or two halogen substituents, for example chlorine substituents;

$Het^3-S(O)_2$—, wherein in one embodiment $Het^3-S(O)_2$— is pyrrolidinyl-SO$_2$—; $Het^2$, wherein in one embodiment $Het^2$ is morpholinyl;

$(C_1-C_4)$-alkyl which is substituted by one or more fluorine substituents, wherein in one embodiment such fluorine-substituted $(C_1-C_4)$-alkyl is $(C_1-C_4)$-perfluoroalkyl and in another embodiment is trifluoromethyl, i.e. $F_3C$—;

$(C_1-C_4)$-alkyl-O— which is substituted by one or more fluorine substituents, wherein in one embodiment such fluorine-substituted $(C_1-C_4)$-alkyl-O— is $(C_1-C_4)$-perfluoroalkyl-O— and in another embodiment is trifluoromethoxy, i.e. $F_3C$—O—;

and either the groups $R^1$ and $R^2$, or the groups $R^2$ and $R^3$, or the groups $R^3$ and $R^4$ form, together with the carbon atoms carrying them, can form a benzene ring or a 5-membered to 7-membered cycloalkane ring, wherein in one embodiment such a ring is a benzene ring or a cyclopentane or cyclohexane ring, and in another embodiment a benzene ring or a cyclohexane ring, and wherein in one embodiment a benzene ring formed by two groups $R^1$, $R^2$, $R^3$ and $R^4$ is unsubstituted or substituted by one or more, for example one or two, identical or different substituents selected from the series consisting of halogen and $(C_1-C_4)$-alkyl, and a cycloalkane ring formed by two groups $R^1$, $R^2$, $R^3$ and $R^4$ is unsubstituted or substituted by one or more, for example one or two, identical or different substituents selected from the series consisting of fluorine and $(C_1-C_4)$-alkyl, and in another embodiment a ring formed by two groups $R^1$, $R^2$, $R^3$ and $R^4$ is unsubstituted.

In general is the carbocyclic ring which can be formed by either the groups $R^1$ and $R^2$, or the groups $R^2$ and $R^3$, or the groups $R^3$ and $R^4$, together with the carbon atoms carrying them in one embodiment selected from the series consisting of benzene, cyclopentane and cyclohexane, in another embodiment from the series consisting of benzene and cyclohexane. Since in the case of a cycloalkane ring formed by two groups $R^1$, $R^2$, $R^3$ and $R^4$ the double bond between the two carbon atoms common to both fused rings may be regarded as being contained in both rings, such a cycloalkane ring may also be regarded as a cycloalkene ring. In one embodiment, a carbocyclic ring formed by two groups $R^1$, $R^2$, $R^3$ and $R^4$ is unsubstituted or substituted by one or two identical or different substituents, in another embodiment it is unsubstituted. In one embodiment, $R^1$, $R^2$, $R^3$ and $R^4$ have any of their meanings, except that two groups $R^1$, $R^2$, $R^3$ and $R^4$ together with the carbon atoms carrying them do not form a carbocyclic ring.

In one embodiment, one of the groups $R^1$, $R^2$, $R^3$ and $R^4$ is hydrogen and the others have any of their specified meanings, in another embodiment two of the group $R^1$, $R^2$, $R^3$ and $R^4$ are hydrogen and the others have any of their specified meanings.

In one embodiment compounds of the formula I are defined as above and $R^5$ is selected from the series consisting of hydrogen and methyl, and in another embodiment $R^5$ is hydrogen.

In one embodiment compounds of the formula I are defined as above and $R^{11}$, $R^{12}$, $R^{13}$, $R^{14}$ and $R^{15}$ are independently of each other selected from the series consisting of hydrogen, methyl and ethyl, in another embodiment from the series consisting of hydrogen and methyl, and in another embodiment they are hydrogen.

In one embodiment, a $(C_3-C_8)$-cycloalkyl group representing $Z^1$ or $Z^2$ is a $(C_4-C_8)$-cycloalkyl group, in another embodiment a $(C_5-C_8)$-cycloalkyl group, in another embodiment a $(C_5-C_7)$-cycloalkyl group, in another embodiment a $(C_6-C_7)$-cycloalkyl group, in another embodiment a cyclohexyl group, which are all unsubstituted or substituted as specified. In one embodiment, the number of substituents in a substituted cycloalkyl group and in a substituted phenyl group representing $Z^1$ or $Z^2$ independently of one another is one, two, three or four, in another embodiment it is one, two or three, in another embodiment it is one or two, in another embodiment it is one, in another embodiment it is zero. In one embodiment, a cycloalkyl group representing $Z^1$ or $Z^2$ is unsubstituted. In one embodiment, the substituents in a substituted cycloalkyl group representing $Z^1$ or $Z^2$ are selected from the series consisting of fluorine and $(C_1-C_4)$-alkyl, in another embodiment from the series consisting of $(C_1-C_4)$-alkyl and $(C_1-C_4)$-alkyl-O—, and in another embodiment they are $(C_1-C_4)$-alkyl substituents. In one embodiment, the substituents in a substituted phenyl group representing $Z^1$ or $Z^2$ are selected from the series consisting of halogen, $(C_1-C_4)$-alkyl and $(C_1-C_4)$-alkyl-O—, in another embodiment from the series consisting of halogen and $(C_1-C_4)$-alkyl.

In one embodiment, compounds of the formula I are defined as above and one of the groups $Z^1$ and $Z^2$ is $(C_3-C_8)$-cycloalkyl and the other is selected from the series consisting of hydrogen, $(C_1-C_8)$-alkyl and $(C_3-C_8)$-cycloalkyl, in another embodiment one of the groups $Z^1$ and $Z^2$ is $(C_3-C_8)$-cycloalkyl and the other is selected from the series consisting of hydrogen, $(C_3-C_8)$-cycloalkyl and phenyl, in another embodiment one of the groups $Z^1$ and $Z^2$ is $(C_3-C_8)$-cycloalkyl and the other is selected from the series consisting of hydrogen and $(C_3-C_8)$-cycloalkyl, in another embodiment one of the groups $Z^1$ and $Z^2$ is $(C_3-C_8)$-cycloalkyl and the other is selected from the series consisting of $(C_3-C_8)$-cycloalkyl and phenyl, in another embodiment the groups $Z^1$ and $Z^2$ are identical or different $(C_3-C_8)$-cycloalkyl group, and in another embodiment the groups $Z^1$ and $Z^2$ are identical $(C_3-C_8)$-cycloalkyl groups, wherein all groups are unsubstituted or substituted as specified.

In one embodiment, the number of substituents in a substituted group Ar or in a substituted group $Het^1$ or a substituted groups $Het^2$ or a substituted group $Het^3$ is independently of one another one, two or three, in another embodiment it is one or two, in another embodiment it is one, in another embodiment it is zero. In one embodiment, Ar is phenyl or an aromatic 5-membered or 6-membered, monocyclic heterocycle which comprises one ring heteroatom selected from the series consisting of N, O and S, in another embodiment Ar is selected from the series consisting of phenyl, pyridinyl and thienyl, in another embodiment from the series consisting of phenyl and pyridinyl, and in the another embodiment Ar is phenyl, wherein all groups are unsubstituted or substituted as specified. In one embodiment, the substituents in a substituted group Ar are selected from the series consisting of halogen, $(C_1-C_4)$-alkyl and $(C_1-C_4)$-alkyl-O—, in another embodiment from the series consisting of halogen and $(C_1-C_4)$-alkyl.

In one embodiment, $Het^2$ is a saturated 5-membered or 6-membered, monocyclic heterocycle which comprises one or two identical or different ring heteroatoms selected from the series consisting of N, O and S, in another embodiment from the series consisting of N and O, and in another embodiment $Het^2$ is selected from the series consisting of pyrrolidinyl, tetrahydropyranyl, piperidinyl and morpholinyl, and in another embodiment $Het^2$ is morpholinyl. In one embodiment, $Het^2$ is bonded via a ring carbon atom, in another embodiment via a ring nitrogen atom.

In one embodiment, $Het^3$ is a saturated 5-membered or 6-membered, monocyclic heterocycle which, besides the ring nitrogen atom via which $Het^3$ is bonded, comprises zero or one, in another embodiment zero, further ring heteroatom selected from the series consisting of N, O and S, in another embodiment from the series consisting of N and O, and in another embodiment $Het^3$ is selected from the series consisting of pyrrolidinyl, piperidinyl and morpholinyl, and in another embodiment $Het^2$ is pyrrolidinyl.

In one embodiment, n is selected from the numbers 0 and 2, in another embodiment n is 2.

In one embodiment of the invention, the compound of the formula I is selected from the series consisting of 4,4-Dicyclohexyl-7-pyrrol-1-yl-4H-benzo[1,3]dioxine-2-carboxylic acid,
4,4-Dicyclohexyl-6-methyl-4H-benzo[1,3]dioxine-2-carboxylic acid,
4,4-Dicyclohexyl-7-methoxy-4H-benzo[1,3]dioxine-2-carboxylic acid,
4,4-Dicyclohexyl-6-fluoro-4H-benzo[1,3]dioxine-2-carboxylic acid,
4,4-Dicyclohexyl-7-dimethylamino-4H-benzo[1,3]dioxine-2-carboxylic acid,
4,4-Dicyclohexyl-5,7-dimethoxy-4H-benzo[1,3]dioxine-2-carboxylic acid,
4,4-Dicyclohexyl-4H-naphtho[2,3-d][1,3]dioxine-2-carboxylic acid,
4,4-Dicyclohexyl-7-methyl-4H-benzo[1,3]dioxine-2-carboxylic acid,
4,4-Dicyclohexyl-5-methyl-4H-benzo[1,3]dioxine-2-carboxylic acid,
7-Chloro-4,4-dicyclohexyl-4H-benzo[1,3]dioxine-2-carboxylic acid,
4,4-Dicyclohexyl-8-methyl-4H-benzo[1,3]dioxine-2-carboxylic acid,
4,4-Dicyclohexyl-8-fluoro-4H-benzo[1,3]dioxine-2-carboxylic acid,
6-tert-Butyl-4,4-dicyclohexyl-4H-benzo[1,3]dioxine-2-carboxylic acid,
4,4-Dicyclohexyl-6-iodo-4H-benzo[1,3]dioxine-2-carboxylic acid,
4,4-Dicyclohexyl-6-trifluoromethyl-4H-benzo[1,3]dioxine-2-carboxylic acid,
6-Chloro-4,4-dicyclohexyl-2-methyl-4H-benzo[1,3]dioxine-2-carboxylic acid,
4,4-Dicyclohexyl-6-trifluoromethoxy-4H-benzo[1,3]dioxine-2-carboxylic acid,
6-Chloro-4,4-dicyclohexyl-7-fluoro-4H-benzo[1,3]dioxine-2-carboxylic acid,
6-Chloro-4,4-dicyclohexyl-8-fluoro-4H-benzo[1,3]dioxine-2-carboxylic acid,
6-Chloro-4,4-dicyclohexyl-5-fluoro-4H-benzo[1,3]dioxine-2-carboxylic acid,
6-(4-Chloro-phenoxy)-4,4-dicyclohexyl-4H-benzo[1,3]dioxine-2-carboxylic acid,
4,4-Dicyclohexyl-6-pyridin-4-yl-4H-benzo[1,3]dioxine-2-carboxylic acid,
4,4-Dicyclohexyl-6-(3-methoxy-phenoxy)-4H-benzo[1,3]dioxine-2-carboxylic acid,
6-(3-Chloro-phenoxy)-4,4-dicyclohexyl-4H-benzo[1,3]dioxine-2-carboxylic acid,
6-(4-Chloro-benzoyl)-4,4-dicyclohexyl-4H-benzo[1,3]dioxine-2-carboxylic acid,
4,4-Dicyclohexyl-6-(pyridin-3-yloxy)-4H-benzo[1,3]dioxine-2-carboxylic acid,
4,4-Dicyclohexyl-4H-benzo[1,3]dioxine-2-carboxylic acid,
4,4-Dicyclohexyl-8-methoxy-4H-benzo[1,3]dioxine-2-carboxylic acid,
4,4-Dicyclohexyl-5-ethoxy-4H-benzo[1,3]dioxine-2-carboxylic acid,
7-Butoxy-4,4-dicyclohexyl-4H-benzo[1,3]dioxine-2-carboxylic acid,
6,8-Dichloro-4,4-dicyclohexyl-4H-benzo[1,3]dioxine-2-carboxylic acid,
1,1-Dicyclohexyl-1H-naphtho[2,1-d][1,3]dioxine-3-carboxylic acid,
4,4-Dicyclohexyl-6-methoxy-4H-benzo[1,3]dioxine-2-carboxylic acid,
4,4-Dicyclohexyl-6-phenyl-4H-benzo[1,3]dioxine-2-carboxylic acid,
4,4-Dicyclohexyl-7-methoxy-5-methyl-4H-benzo[1,3]dioxine-2-carboxylic acid,
7-Benzyloxy-4,4-dicyclohexyl-4H-benzo[1,3]dioxine-2-carboxylic acid,
6-Chloro-4,4-dicyclohexyl-7-methoxy-4H-benzo[1,3]dioxine-2-carboxylic acid,
4,4-Dicyclohexyl-6-(pyrrolidine-1-sulfonyl)-4H-benzo[1,3]dioxine-2-carboxylic acid,
4,4-Dicyclohexyl-7-morpholin-4-yl-4H-benzo[1,3]dioxine-2-carboxylic acid,
4,4-Dicyclohexyl-4H-naphtho[1,2-d][1,3]dioxine-2-carboxylic acid,
6-Chloro-4,4-dicyclohexyl-8-methyl-4H-benzo[1,3]dioxine-2-carboxylic acid,
6-Chloro-4,4-dicyclohexyl-7-methyl-4H-benzo[1,3]dioxine-2-carboxylic acid,
4,4-Dicyclohexyl-5,7-difluoro-4H-benzo[1,3]dioxine-2-carboxylic acid, 1,1-Dicyclohexyl-7,8,9,10-tetrahydro-1H-naphtho[2,1-d][1,3]dioxine-3-carboxylic acid,
4,4-Dicyclohexyl-8-trifluoromethoxy-4H-benzo[1,3]dioxine-2-carboxylic acid,
8-tert-Butyl-4,4-dicyclohexyl-4H-benzo[1,3]dioxine-2-carboxylic acid,
10-Benzyl-4,4-dicyclohexyl-4H-naphtho[2,3-d][1,3]dioxine-2-carboxylic acid,
4,4-Dicyclohexyl-7-diethylamino-4H-benzo[1,3]dioxine-2-carboxylic acid,
6-Bromo-4,4-dicyclohexyl-4H-benzo[1,3]dioxine-2-carboxylic acid,
6-Chloro-4,4-dicyclopentyl-4H-benzo[1,3]dioxine-2-carboxylic acid,
6-Chloro-4-cycloheptyl-4H-benzo[1,3]dioxine-2-carboxylic acid,
6-Bromo-4,4-dicyclohexyl-4H-benzo[1,3]dioxine-2-carboxylic acid,
6-Chloro-4,4-dicycloheptyl-4H-benzo[1,3]dioxine-2-carboxylic acid,
6-Chloro-4,4-dicyclooctyl-4H-benzo[1,3]dioxine-2-carboxylic acid,
6-Chloro-4,4-dicycloheptyl-7-methyl-4H-benzo[1,3]dioxine-2-carboxylic acid,
4,4-Dicycloheptyl-6-trifluoromethoxy-4H-benzo[1,3]dioxine-2-carboxylic acid,
6-Bromo-4,4-dicycloheptyl-4H-benzo[1,3]dioxine-2-carboxylic acid,
5-(6-Chloro-4,4-dicyclohexyl-4H-benzo[1,3]dioxin-2-yl)-1H-tetrazole,
3-(6-Chloro-4,4-dicyclohexyl-4H-benzo[1,3]dioxin-2-yl)-4H-[1,2,4]oxadiazol-5-one,
6-Chloro-4,4-dicyclohexyl-4H-benzo[1,3]dioxine-2-carboxylic acid methyl ester, and
5-(6-Chloro-4,4-dicyclohexyl-4H-benzo[1,3]dioxin-2-yl)-3H-[1,3,4]oxadiazol-2-one,
and all stereoisomeric forms thereof and mixtures of stereoisomeric forms in any ratio, and the pharmaceutically acceptable salts thereof.

The substitution pattern in the compounds of the formula I, which may be termed as 4H-benzo[1,3]dioxines or benzo[1,3]dioxanes, for example, and herein are also termed benzodioxanes, is numbered according to IUPAC rules and indicated in the following formula.

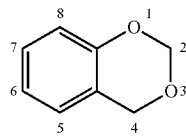

If structural elements such as groups, substituents or numbers, for example alkyl, cycloalkyl or Ar groups or the number n, can occur several times in the compounds of the formula I, they are all independent of each other and can in each case have any of the indicated meanings, and they can in each case be identical to or different from any other such element.

The term alkyl is to be understood as meaning a residue of a saturated acyclic hydrocarbon which can be linear, i.e. straight-chain, or branched. If not otherwise defined, alkyl has 1 to 4 carbon atoms. Examples of $(C_1-C_4)$-alkyl are alkyl residues containing 1, 2, 3 or 4 carbon atoms including methyl, ethyl, propyl, butyl, the n-isomers of these residues, isopropyl, isobutyl, sec-butyl, tert-butyl. All these statements also apply if an alkyl group is substituted or occurs as a substituent on another residue, for example in an alkyl-O— residue (alkyloxy residue, alkoxy residue), an alkyl-O—C(O)— residue (alkyloxycarbonyl residue) or an aryl-alkyl-residue.

The term $(C_3-C_8)$-cycloalkyl is to be understood as meaning a residue of a saturated cyclic hydrocarbon cycle containing from 3 to 8 ring carbon atoms in a monocyclic ring. Examples of $(C_3-C_8)$-cycloalkyl are cycloalkyl residues containing 3, 4, 5, 6, 7 or 8 ring carbon atoms like cyclopropyl, cyclobutyl, cyclopentyl, cyclohexyl, cycloheptyl or cyclooctyl.

The term 5-membered to 7-membered cycloalkane is to be understood as meaning cyclopentane, cyclohexane or cycloheptane.

The term Ar is to be understood as meaning phenyl or a residue of an aromatic, 5-membered or 6-membered, monocyclic hydrocarbon ring, wherein in the said hydrocarbon ring one or two ring carbon atoms are replaced by identical or different ring heteroatoms selected from the series consisting of N, O and S, such as furanyl, pyridinyl, oxazolyl, isoxazolyl, thiazolyl, isothiazolyl, imidazolyl, pyrazinyl, pyridazinyl, pyrimidinyl, pyrrolyl, pyrazolyl and thienyl residues, which are all unsubstituted or substituted by one or more, for example by one, two or three, or by one or two, or by one, identical or different substituents selected from the series consisting of halogen, $(C_1-C_4)$-alkyl, cyano, $(C_1-C_4)$-alkyl-O— and $(C_1-C_4)$-alkyl-S(O)$_n$—.

The term Het$^1$ is to be understood as meaning a residue of partially unsaturated or aromatic, 5-membered or 6-membered, monocyclic hydrocarbon ring, wherein one to four ring carbon atoms are replaced by identical or different ring heteroatoms selected from the series consisting of N, O and S, such as furanyl, pyridinyl, oxazolyl, isoxazolyl, thiazolyl, isothiazolyl, imidazolyl, pyrazinyl, pyridazinyl, pyrimidinyl, pyrrolyl, pyrazolyl and thienyl, 1,2,4,5-tetrazinyl, 1,2,3,4-tetrazinyl, 1,2,3-triazinyl, 1,2,4-triazinyl, 1,3,5-triazinyl, tetrazolyl, thiadiazolyl, 1,2,3-triazolyl and 1,2,4-triazolyl, 1,2,4-oxadiazolyl, 1,3,4-oxadiazolyl, pyranyl, 1,2-oxazinyl, 1,3-oxazinyl, 1,4-oxazinyl, 1,2-thiazine, 1,3-thiazine, 1,4-thiazine, pyrrolinyl, thiadiazinyl and thiazolinyl, which can be unsubstituted or substituted by one or more, for example by one, two or three, or by one or two, or by one, identical or different substituents selected from the series consisting of $(C_1-C_4)$-alkyl, hydroxy and oxo and which is bonded via a ring carbon atom.

The term Het$^2$ is to be understood as meaning a residue of a saturated, 4-membered, 5-membered, 6-membered or 7-membered, monocyclic hydrocarbon ring, wherein one or two ring carbon atoms are replaced by identical or different ring heteroatoms selected from the series consisting of N, O and S, such as oxetanyl, azetidinyl, thietanyl, dioxetanyl, morpholinyl, thiomorpholinyl, piperazinyl, piperidinyl, pyrrolidinyl, oxazolidinyl, thiazolidinyl, 1,2-oxathiolanyl, 1,3-oxathiolanyl, tetrahydrofuranyl and tetrahydropyranyl, which can be bonded via a ring carbon atom or a ring nitrogen atom, and which is unsubstituted or substituted by one or more, for example by one, two or three, or by one or two, or by one, identical or different substituents selected from the series consisting of fluorine and $(C_1-C_4)$-alkyl.

The term Het$^3$ is to be understood as meaning a residue of a saturated, 4-membered, 5-membered, 6-membered or 7-membered, monocyclic hydrocarbon ring, which comprises a ring nitrogen atom via which Het$^3$ is bonded and wherein zero or one further ring carbon atom is replaced by a heteroatom selected from the series consisting of N, O and S, such as azetidinyl, morpholinyl, thiomorpholinyl, piperazinyl, piperidinyl, pyrrolidinyl, thiazolidinyl and oxazolidinyl, and which is unsubstituted or substituted by one or more, for example by one, two or three, or by one or two, or by one, identical or different substituents selected from the series consisting of fluorine and $(C_1-C_4)$-alkyl.

Alkyl groups can in general, independently of any other substituents which an alkyl groups carries, be unsubstituted or substituted by one or more fluorine substituents, for example by one, two, three, four or five fluorine substituents, or by one, two or three fluorine substituents. Such fluorine-substituted alkyl group can also be perfluoroalkyl groups, i.e. alkyl groups in which all hydrogen atoms are replaced by fluorine atoms. Examples of fluorine-substituted alkyl groups are $—CF_3$, $—CHF_2$, $—CH_2F$ and $—CF_2—CF_3$, of which $—CF_3$ and $—CF_2—CF_3$ are examples of perfluoroalkyl groups. In one embodiment, an alkyl group in any occurrence, independently of other occurrences, and independently of any other substituents which the alkyl groups carries, is not substituted by fluorine.

Halogen is fluorine, chlorine, bromine or iodine. In one embodiment, halogen is in any of its occurrences, independently of other occurrences, selected from the series consisting of fluorine, chlorine an bromine, in another embodiment from the series consisting of fluorine and chlorine.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers in any ratio, for example in the form of racemates. Thus, the present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers), the invention relates both to pure E isomers and pure Z isomers and to E/Z (or cis/trans) mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Pharmaceutically acceptable salts of the compounds of the formula I are understood to be nontoxic salts that are physiologically acceptable and in particular pharmaceutically utilizable salts. Such salts of compounds of the formula I containing acidic groups, for example a carboxylic acid group COOH, are for example alkali metal salts or alkaline earth metal salts such as sodium salts, potassium salts, magnesium salts and calcium salts, and also salts with pharmaceutically acceptable quaternary ammonium ions such as tetramethylammonium or tetraethylammonium, and acid addition salts with ammonia and pharmaceutically acceptable organic amines, such as methylamine, dimethylamine, trimethylamine, ethylamine, triethylamine, ethanolamine or tris-(2-hydroxyethyl)amine. Basic groups contained in the compounds of the formula I, for example amino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I which simultaneously contain a basic group and an acidic group, for example an amino group and a carboxyl group, can also be present as zwitterions (betaines), which are likewise included in the present invention.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of pharmaceutically acceptable salts.

The invention also includes solvates, derivatives and modifications of the compounds of the formula I, for example prodrugs, protected forms and other pharmaceutically acceptable derivatives. In particular the invention relates to prodrugs and protected forms of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; H. Bundgaard, Drugs of the Future 16 (1991) 443; Hydrolysis in Drug and Prodrug Metabolism, B. Testa, J. M. Mayer, Wiley-VCH, 2003.

Suitable prodrugs for the compounds of the formula I are especially acyl prodrugs and carbamate prodrugs of acylatable nitrogen-containing groups such as amino groups and ester prodrugs and amide prodrugs of carboxylic acid groups which may be present in compounds of the formula I. In the acyl prodrugs and carbamate prodrugs a hydrogen atom on a nitrogen atom in such groups is replaced with an acyl group or an ester group, for example a $(C_1-C_6)$-alkyl-O—C(O)— group. Suitable acyl groups and ester groups for acyl prodrugs and carbamate prodrugs are, for example, the groups $R^{p1}$—CO— and $R^{p2}$O—CO—, wherein $R^{p1}$ can be hydrogen, $(C_1-C_4)$-alkyl, $(C_3-C_8)$-cycloalkyl, $(C_3-C_8)$-cycloalkyl-$(C_1-C_4)$-alkyl-, Ar, $(C_6-C_{14})$-aryl, $Het^1$, $Het^2$, $(C_6-C_{14})$-aryl-$(C_1-C_4)$-alkyl-, Ar—$(C_1-C_4)$-alkyl-, $Het^1$-$(C_1-C_4)$-alkyl-, $Het^2$-$(C_1-C_4)$-alkyl- or $Het^3$-$(C_1-C_4)$-alkyl-, for example, and wherein $R^{p2}$ has the meanings indicated for $R^{p1}$ with the exception of hydrogen. The term $(C_6-C_{14})$-aryl is understood as meaning a residue of a monocyclic, bicyclic or tricyclic aromatic hydrocarbon containing from 6 to 14 ring carbon atoms, for example 6, 7, 8, 9, 10, 11, 12, 13 or 14 ring carbon atoms. Examples are phenyl, naphthyl, for example 1-naphthyl and 2-naphthyl, or biphenylyl.

Also with respect to all embodiments of the invention specified herein it applies that the comprised compounds of the formula I are a subject of the invention in all their stereoisomeric forms and mixtures of stereoisomeric forms in any ratio, and in the form of their pharmaceutically acceptable salts, as well as in the form of their prodrugs.

The present invention also relates to processes for the preparation of the compounds of the formula I, by which the compounds are obtainable and which are another subject of the invention.

The compounds of the formula I can be prepared by utilizing procedures and techniques, which per se are well known and appreciated by one of ordinary skill in the art. Starting materials or building blocks for use in the general synthetic procedures that can be applied in the preparation of the compounds of the formula I are readily available to one of ordinary skill in the art. In many cases they are commercially available or have been described in the literature. Otherwise they can be prepared from readily available precursor compounds analogously to procedures described in the literature, or by procedures or analogously to procedures described herein.

In general, compounds of the formula I can be prepared, for example, in the course of a convergent synthesis, by linking two or more fragments which can be derived retrosynthetically from the formula I. More specifically, suitably substituted starting 2-hydroxymethyl-phenol derivatives are employed as precursor building blocks in the preparation of the benzodioxane compounds of the formula I and reacted with suitably substituted alkanoic acids or alkanoic acid derivatives. For example, 2-hydroxymethyl-phenol derivatives of the formula II can be reacted with alkanoic acids or alkanoic acid derivatives of the formula III, which carry two monovalent leaving groups or a divalent oxo group in position 2, such as a 2,2-dichloro-alkanoic acid or derivative thereof like 2,2-dichloro-acetic acid in case the group A' is hydrogen, to give a compound of the formula I', which can already be the final compound of the formula I or in which further modifications can be made to give the final compound of the formula I.

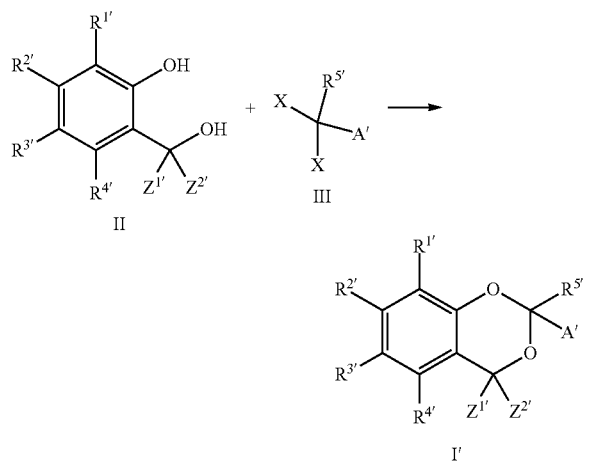

The groups A', $R^{1'}$ to $R^{5'}$, $Z^{1'}$ and $Z^{2'}$ in the compounds of the formula II, III and I' are defined as in the compounds of the formula I, and additionally functional groups can be present in protected form or in the form of precursor groups which are subsequently converted into the final groups present in the compound of the formula I. The groups X in the compounds of the formula III are suitable monovalent leaving groups, for example halogen like chlorine, or together are an oxygen atom, i.e. form a divalent oxo group, for example.

If not commercially available, such 2-hydroxymethyl-phenol derivatives employed in the synthesis of the compound of the formula I can be prepared according to the well-known standard procedures for the formation of 2-hydroxymethyl-phenol systems. By choosing suitable precursor molecules, these 2-hydroxymethyl-phenol syntheses allow the introduction of a variety of substituents into the various positions of the 2-hydroxymethyl-phenol system, which can be chemically modified in order to finally arrive at the compound of the formula I having the desired substituent pattern.

If starting 2-hydroxymethyl-phenol derivatives are not commercially available and have to be synthesized, this can be done via a variety of well known methods. In the following, some procedures of interest for the synthesis of the compounds of the invention are briefly listed and referenced in an exemplary manner. They illustrate some of the possible ways to access suitable 2-hydroxymethyl-phenol derivatives.

1. Humbert et al., Eur. J. Med. Chem. 1983, 18, 67-78.

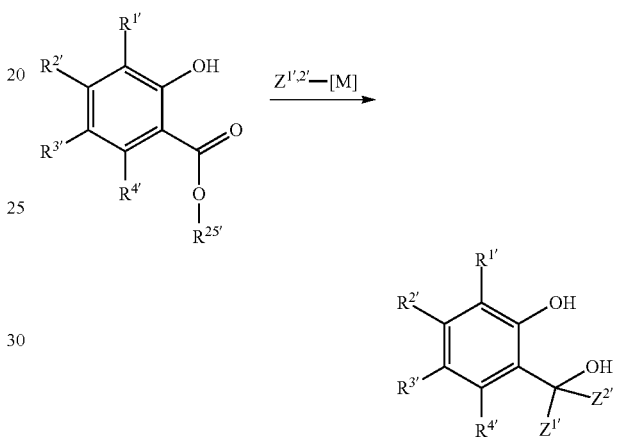

2. Blechert et al., Tetrahedron 1995, 51, 1167-1176.

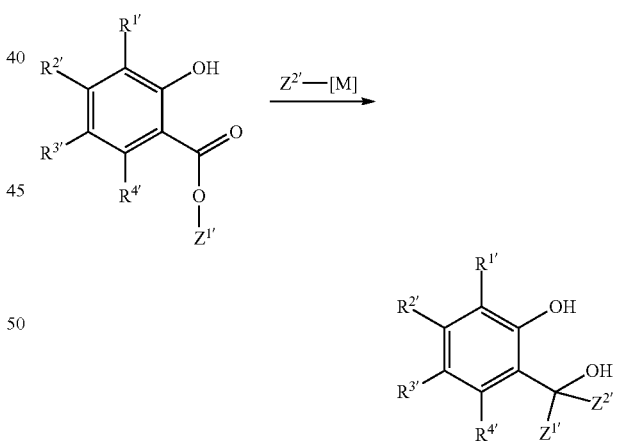

3. J. Talley et al., J. Org. Chem. 1984, 49, 5267-5269.

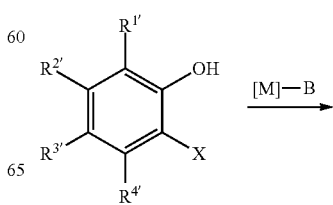

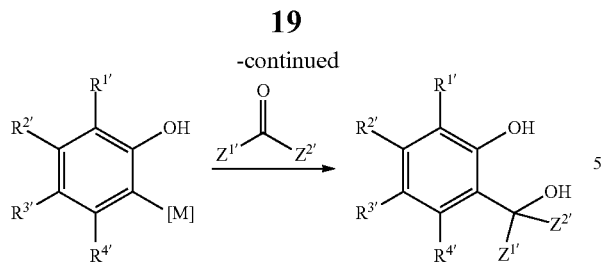

4. Hoppe et al., Synthesis 2006, 1578-1589.

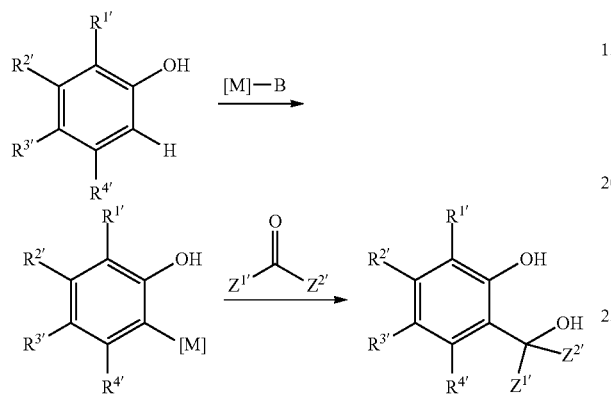

In the following, some procedures for accessing the benzodioxanes derivatives of the formula I from a suitable 2-hydroxymethyl-phenol derivative by subsequent ring closure step to benzodioxane derivatives, which are of interest for the preparation of the compound of the invention, are briefly listed and referenced in an exemplary manner.

5. Wang et al., Org. Lett. 2007, 9, 1533-1535.

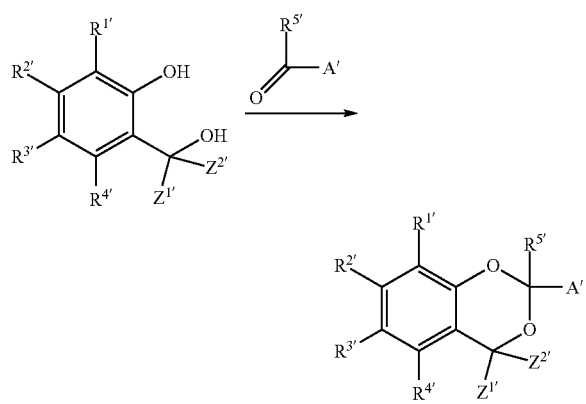

6. Humbert et al., Eur. J. Med. Chem. 1983, 18, 67-78.

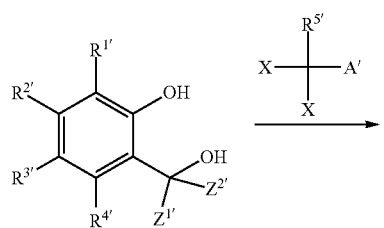

7. Yus et al., Tetrahedron 1997, 53, 17373-17382.

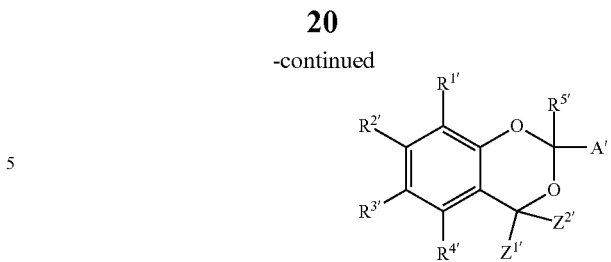

8. Njarddarson et al., Synlett 2009, 23-27.

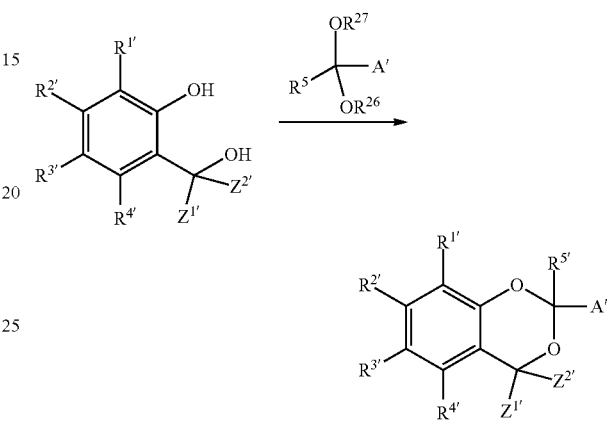

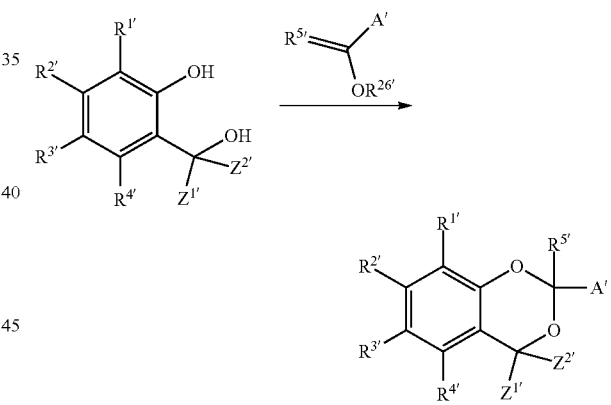

These methods are standard procedures comprehensively discussed in the literature, and are well known to one skilled in the art. It is within the abilities of a person skilled in the art to replace the exemplary compounds and reagents shown in the schemes by appropriate alternative compounds or reagents or to omit or add synthetic steps when appropriate. Although not always shown explicitly, in certain cases positional isomers will occur during the synthesis by the mentioned reactions. Such mixtures of positional isomers can be separated by modern separation techniques like, for example, preparative HPLC. The residues in the formulae shown above can already contain the desired final groups, i.e. the groups $R^1$, $R^{2'}$, $R^{3'}$, $R^{4'}$, $R^{5'}$, $Z^{1'}$, $Z^{2'}$, and A' can be the groups as defined in the formula I, or optionally these residues can be converted into the final groups to give the desired compound of the formula I. The residues of the formulae shown above can also be present in the form of groups that can subsequently be transformed into the final groups and. for example, functional groups can be present in the form of precursor groups or of derivatives or in protected form.

Further, in order to obtain the desired substituents at the benzodioxane ring system in the formula I, the functional groups introduced into the ring system during the benzodioxane synthesis can be chemically modified. Especially the substituents present on the benzodioxane ring system can be modified by a variety of reactions and thus the desired residues can be obtained. For example, a benzodioxane carrying a hydrogen atom in a certain position can also be obtained by saponification and subsequent decarboxylation of a benzodioxane carrying an ester group in that position. Halogen atoms can be introduced, for example according to well-known procedures described in the literature. The fluorination of aromatic substructures of compounds of the formula I can be carried out using a variety of reagents including, for example, N-fluoro-2,4,6-trimethylpyridinium triflate. Chlorinations, brominations, or iodinations can be accomplished by reaction with the elemental halogens or by the use of N-halo-succinimides like NCS, NBS or NIS and many other reagents well known to those skilled in the art. Depending on the reaction conditions, reagent, stoichiometry and substitution pattern, the halogen is introduced in certain positions. By selective halogen/metal exchange in the obtained compounds, like by metalation by selective hydrogen/metal exchange, and subsequent reaction with a wide range of electrophiles various substituents can be introduced at the cyclic nucleus using procedures well-known to those skilled in the art.

Halogens, hydroxy groups (via the triflate or nonaflate) or primary amines (via the diazonium salt), or after interconversion the corresponding stannanes or boronic acids, present in the benzodioxane structure can be converted into a variety of other functional groups like for example —CN, —CF$_3$, —C$_2$F$_5$, ethers, acids, amides, amines, alkyl or aryl groups mediated by means of transition metals, such as palladium or nickel catalysts or copper salts and reagents for example referred to below (F. Diederich, P. Stang, Metal-catalyzed Cross-coupling Reactions, Wiley-VCH, 1998; M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. 1998, 110, 2154; B. Yang, S. Buchwald, J. Organomet. Chem. 1999, 576, 125; T. Sakamoto, K. Ohsawa, J. Chem. Soc. Perkin Trans I, 1999, 2323; D. Nichols, S. Frescas, D. Marona-Lewicka, X. Huang, B. Roth, G. Gudelsky, J. Nash, J. Med. Chem, 1994, 37, 4347; P. Lam, C. Clark, S. Saubern, J. Adams, M. Winters, D. Chan, A. Combs, Tetrahedron Lett., 1998, 39, 2941; D. Chan, K. Monaco, R. Wang, M. Winters, Tetrahedron Lett. 1998, 39, 2933; V. Farina, V. Krishnamurthy, W. Scott, The Stille Reaction, Wiley, 1994; F. Qing et al. J. Chem. Soc. Perkin Trans. 11997, 3053; S. Buchwald et al., J. Am. Chem. Soc. 2001, 123, 7727; S. Kang et al. Synlett 2002, 3, 427; S. Buchwald et al., Organic Lett. 2002, 4, 581; T. Fuchikami et al. Tetrahedron Lett. 1991, 32, 91; Q. Chen et al. Tetrahedron Lett. 1991, 32, 7689; M. R. Netherton, G. C. Fu, Topics in Organometallic Chemistry 2005, 14, 85-108; A. F. Littke, G. F. Fu, Angew. Chem. Int. Ed. 2002, 41, 4176-4211; A. R. Muci, S. L. Buchwald, Topics in Current Chemistry 2002, 219, 131-209).

For example, nitro groups can be reduced to amino groups with various reducing agents, such as sulfides, dithionites, complex hydrides or by catalytic hydrogenation. A reduction of a nitro group may be carried out at various stages of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce these residues, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the benzodioxane nucleus can be hydrolyzed to the corresponding carboxylic acids, which after activation can then be reacted with amines or alcohols under standard conditions. Furthermore, these ester or acid groups can be reduced to the corresponding alcohols by many standard procedures. Ether groups, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

Groups in the benzodioxanes of the formula I, which may also be present in protected form or in the form of a precursor group, which have not already been introduced during a preceding step, for example during a synthesis of the benzodioxane nucleus, can be introduced, for example in the 7-position of the benzodioxane system, for example by standard alkylation procedures well-known to one skilled in the art. The starting benzodioxane derivative that is to be employed in such a reaction carries, for example, an oxygen or a nitrogen or a sulfur atom in the 7-position. Alkylation of the aforementioned atom can, for example, be performed under standard conditions, preferably in the presence of a base like K$_2$CO$_3$, Cs$_2$CO$_3$, NaH or KOtBu, using an alkylating reagent containing a leaving group, like for example halogen like chlorine, bromine or iodine, or a sulfonyloxy group like tosyloxy, mesyloxy or trifluormethylsulfonyloxy. These standard procedures are for example described in treatises like M. Smith, J. March, March's Advanced Organic Chemistry, Wiley-VCH, 2001; Houben-Weyl, Methoden der Organischen Chemie (Methods of Organic Chemistry), Georg Thieme Verlag, Stuttgart, Germany; Organic Reactions, John Wiley & Sons, New York; R. C. Larock, Comprehensive Organic Transformations, Wiley-VCH, 2$^{nd}$ ed., 1999; B. Trost, I. Fleming (eds.), Comprehensive Organic Synthesis, Pergamon, 1991. A leaving group may, for example, also be a hydroxy group which, in order to achieve the alkylation reaction, is activated under the well-known conditions of the Mitsunobu procedure (0. Mitsunobu, Synthesis 1981, 1) or by further modified procedures (A. Tunoori, D. Dutta, G. Gunda, Tetrahedron Lett. 39 (1998) 8751; J. Pelletier, S. Kincaid, Tetrahedron Lett. 41 (2000) 797; D. L. Hughes, R. A. Reamer, J. J. Bergan, E. J. J. Grabowski, J. Am. Chem. Soc. 110 (1998) 6487; D. J. Camp, I. D. Jenkins, J. Org. Chem. 54 (1989) 3045; D. Crich, H. Dyker, R. J. Harris, J. Org. Chem. 54 (1989) 257).

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, Methoden der Organischen Chemie (Methods of Organic Chemistry), Georg Thieme Verlag, Stuttgart, Germany; Organic Reactions, John Wiley & Sons, New York; R. C. Larock, Comprehensive Organic Transformations, Wiley-VCH, 2$^{nd}$ ed., 1999; B. Trost, I. Fleming (eds.), Comprehensive Organic Synthesis, Pergamon, 1991; A. Katritzky, C. Rees, E. Scriven, Comprehensive Heterocyclic Chemistry II, Elsevier Science, 1996, in which details on the reactions and primary source literature can be found. Due to the fact that in the present case the functional groups are attached to a benzodioxane ring it may in certain cases become necessary to specifically adapt reaction conditions or to choose specific reagents from a variety of reagents that can in principle be employed in a conversion reaction, or otherwise to take specific measures for achieving a desired conversion, for example to use protection group techniques. However, finding suitable reaction variants and reaction conditions in such cases does not cause any problems for one skilled in the art.

The structural elements present in the residues in the 4-position, 5-position, 6-position, 7-position and the 8-position of the benzodioxane ring in the compounds of the formula I can also be introduced, for example into the 2-hydroxymethylphenol precursor or the benzodioxane, using the methods outlined herein by consecutive reaction steps using parallel synthesis methodologies using procedures which per se are well known to one skilled in the art.

In the course of the preparation of the compounds of the formula I it can generally be advantageous or necessary to introduce functional groups which reduce or prevent undesired reactions or side reactions in the respective synthesis steps, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991; or P. Kocienski, Protecting Groups, Thieme, 1994). Examples of precursor groups are cyano groups and nitro groups. The cyano group can, in a later step, be transformed into carboxylic acid derivatives, or by reduction into aminomethyl groups. Nitro groups may be transformed by reduction like catalytic hydrogenation into amino groups. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with trifluoroacetic acid (TFA) or other acids at a later stage of the synthesis.

The compounds of the formula I are effective LPAR5 antagonists which antagonize the effect of endogenous LPA on its LPAR5 receptor. In particular are the compounds of the formula I effective platelet, mast cell and microglial cell LPA receptor LPAR5 antagonists. The compounds of the invention antagonize the platelet aggregating effect of the activation of the platelet LPA receptor LPAR5, the LPA-mediated activation of human mast cells and the LPA-mediated activation of microglia cells. In addition, the compounds of the formula I of the invention also have further advantageous properties, for instance stability in plasma and liver and selectivity versus other receptors whose agonism or antagonism is not intended. This good selectivity, for example, makes it possible to reduce potential side effects existing with regard to molecules having inadequate selectivity.

A subject of the present invention also are the compounds of the formula I and/or the pharmaceutically acceptable salts thereof and/or prodrugs thereof for use as a medicament or as a pharmaceutical, and pharmaceutical compositions which comprise an effective amount of at least one compound of the formula I and/or a pharmaceutical acceptable salt thereof and/or a prodrug thereof and a pharmaceutically acceptable carrier, i.e. one or more pharmaceutically acceptable carrier substances or excipients and/or auxiliary substances or additives, and can be employed in human, veterinary or phytoprotective use.

The activity of the compounds of the formula I can be determined, for example, in the assays described below or in other in vitro or ex vivo assays known to those skilled in the art. The ability of the compounds to inhibit LPA-induced aggregation of platelets may be measured by methods similar to those described in the literature (for example, Holub and Waston in Platelets: A Practical Approach, pp 236-239, Oxford University Press 1996), and by the methods described below. The results of these assays clearly demonstrate that the compounds of the invention are functional antagonists of the platelet LPA receptor LPAR5 and are therefore useful for inhibiting platelet aggregation and thrombus formation. The ability of the compounds to inhibit LPA-induced activation of mast cells or microglial cells may also be measured by using the FLIPR system.

As LPA receptor LPAR5 antagonists, the compounds of the formula I and/or their pharmaceutically acceptable salts and/or their prodrugs are generally suitable for the treatment, including therapy and prophylaxis, of conditions in which the activity of LPAR5 receptor plays a role or has an undesired extent, or which can favorably be influenced by inhibiting LPAR5 receptors or decreasing the activity, or for the prevention, alleviation or cure of which an inhibition of LPA receptor LPAR5 or a decrease in the activity is desired by the physician.

Thus, a subject of the invention also are the compounds of the formula I and/or the pharmaceutically acceptable salts thereof and/or the prodrugs thereof for the use in the treatment, including therapy and prophylaxis, of a disease or disease state responsive to the inhibition of the LPA receptor LPAR5 and/or the reduction or inhibition of platelet aggregation or thrombus formation and/or the reduction or inhibition of the activation of mast cells and/or the reduction or inhibition of the activation of microglial cells.

A subject of the invention also is the use of a compound of the formula I and/or the pharmaceutically acceptable salts thereof and/or the prodrugs thereof for the manufacture of a medicament for the treatment, including therapy and prophylaxis, of a disease or disease state responsive to the inhibition of the LPA receptor LPAR5 and/or the reduction or inhibition of platelet aggregation or thrombus formation and/or the reduction or inhibition of the activation of mast cells and/or the reduction or inhibition of the activation of microglial cells.

A subject of the invention also are the specific compounds of the formula I which are excluded from the compounds which are a subject of the invention as compounds per se, i.e. 6-chloro-4-cyclohexyl-4-phenyl-4H-benzo[1,3]dioxine-2-carboxylic acid, 6-chloro-4-cyclohexyl-4-phenyl-4H-benzo[1,3]dioxine-2-carboxylic acid methyl ester and 6-chloro-4,4-dicyclohexyl-4H-benzo[1,3]dioxine-2-carboxylic acid, and the pharmaceutically acceptable salts thereof and the prodrugs thereof, for the use in the treatment, including therapy and prophylaxis, of a disease or disease state responsive to the inhibition of the LPA receptor LPAR5 and/or the reduction or inhibition of platelet aggregation or thrombus formation and/or the reduction or inhibition of the activation of mast cells and/or the reduction or inhibition of the activation of microglial cells, and all other diseases mentioned above or below herein. A subject of the invention also is the use of the compounds of the formula I which are excluded from the compounds which are a subject of the invention as compounds per se, i.e. 6-chloro-4-cyclohexyl-4-phenyl-4H-benzo[1,3]dioxine-2-carboxylic acid, 6-chloro-4-cyclohexyl-4-phenyl-4H-benzo[1,3]dioxine-2-carboxylic acid methyl ester and 6-chloro-4,4-dicyclohexyl-4H-benzo[1,3]dioxine-2-carboxylic acid, and the pharmaceutically acceptable salts thereof and the prodrugs thereof, for the manufacture of a medicament for the treatment, including therapy and prophylaxis, of a disease or disease state responsive to the inhibition of the LPA receptor LPAR5 and/or the reduction or inhibition of platelet aggregation or thrombus formation and/or the reduction or inhibition of activation of mast cells and/or the reduction or inhibition of activation of microglial cells, and all other diseases mentioned above or below herein.

As inhibition of the LPA receptor LPAR5 influences platelet activation and platelet aggregation, the compounds of the formula I and/or their pharmaceutically acceptable salts and/or their prodrugs are generally suitable for reducing blood thrombus formation, or for the treatment, including therapy and prophylaxis, of conditions and diseases in which the activity of the platelet aggregation plays a role or has an undesired extent, or which can favorably be influenced by reducing thrombus formation, or for the prevention, alleviation or cure of which a decreased activity of the platelet aggregation system is desired by the physician. A specific subject of the present invention thus is the reduction or inhibition of unwanted thrombus formation, in particular in an individual, by administering an effective amount of a compound of the formula I and/or a pharmaceutically acceptable salt and/or a prodrug thereof, as well as pharmaceutical compositions therefore.

As inhibition of the LPA receptor LPAR5 influences mast cell activation the compounds of the formula I and/or their pharmaceutically acceptable salts and/or their prodrugs are generally suitable for reducing mast cell activation, or for the treatment, including therapy and prophylaxis, of conditions in which the activity mast cells plays a role or has an undesired extent, or which can favorably be influenced by reducing mast cell activation, or for the prevention, alleviation or cure of which a decreased activity of the mast cell system is desired by the physician. A specific subject of the present invention thus is the reduction or inhibition of unwanted activation of mast cells, in particular in an individual, by administering an effective amount of a compound of the formula I and/or a pharmaceutically acceptable salt and/or a prodrug thereof, as well as pharmaceutical compositions therefore.

As inhibition of the LPA receptor LPAR5 influences microglial cell activation the compounds of the formula I and/or their pharmaceutically acceptable salts and/or their prodrugs are generally suitable for reducing microglial cell activation, or for the treatment, including therapy and prophylaxiss of conditions in which the activity of microglial cells plays a role or has an undesired extent, or which can favorably be influenced by reducing microglial cell activation, or for the prevention, alleviation or cure of which a decreased activity of the microglial cell system is desired by the physician. A specific subject of the present invention thus is the reduction or inhibition of unwanted activation of microglial cell, in particular in an individual, by administering an effective amount of a compound of the formula I and/or a pharmaceutically acceptable salt and/or a prodrug thereof, as well as pharmaceutical compositions therefore.

The present invention also relates to the compounds of the formula I and/or their pharmaceutically acceptable salts and/or their prodrugs for the use in the treatment, including therapy and prophylaxis, of thromboembolic diseases, such as deep vein thrombosis, venous and arterial thromboembolism, thrombophlebitis, coronary and cerebral arterial thrombosis, cerebral embolism, renal embolism, pulmonary embolism, disseminated intravascular coagulation, cardiovascular disorders, such as transient ischemic attacks, strokes, acute myocardial infarction, peripheral vascular disease, preeclampsia/eclampsia, and thrombotic cytopenic purpura and development and progression of inflammatory disorders, such as hyperalgesia, asthma, multiple sclerosis, inflammatory pain, angiogenesis or allergic responses, or restenoses.

The present invention also relates to the use of the compounds of the formula I and/or their pharmaceutically acceptable salts and/or their prodrugs for the manufacture of pharmaceutical compositions or medicaments for inhibition of the LPA receptor LPAR5 or for influencing platelet activation, platelet aggregation and platelet degranulation and promote platelet disaggregation, inflammatory response and/or for the treatment, including therapy and prophylaxis, of the diseases mentioned above or below, for example for the production of medicaments for the therapy and prophylaxis of cardiovascular disorders, thromboembolic diseases, restenosis, deep vein thrombosis, venous and arterial thromboembolism, thrombophlebitis, coronary and cerebral arterial thrombosis, cerebral embolism, renal embolism, pulmonary embolism, disseminated intravascular coagulation, transient ischemic attacks, strokes, acute myocardial infarction, peripheral vascular disease, preeclampsia/eclampsia, and thrombotic cytopenic purpura and development and progression of inflammatory disorders, such as hyperalgesia, asthma, multiple sclerosis, angiogenesis, allergic responses and others.

The invention also relates to the compounds of the formula I and/or their pharmaceutically acceptable salts and/or their prodrugs for the use in the treatment, including therapy and prophylaxis, of the diseases mentioned above or below, for example for use in the therapy and prophylaxis of cardiovascular disorders, thromboembolic diseases or restenoses, and to methods of treatment aiming at such purposes including methods for said therapies and prophylaxis.

Due to the central role of the platelet LPA receptor LPAR5 in LPA-mediated activation of platelets, the invention also relates to compounds of the formula I and/or the pharmaceutically acceptable salts thereof for the use in the treatment, including therapy and prophylaxis, of disease states such as abnormal thrombus formation, acute myocardial infarction, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, certain viral infections or cancer. The invention also relates to the use of a compound of the formula I and/or the pharmaceutically acceptable salts thereof for the manufacture of a medicament for the treatment, including therapy and prophylaxis, of said disease states.

Due to the central role of the LPA receptor LPAR5 in LPA-mediated activation of mast cells and/or microglia cells, the invention also relates to compounds of the formula I and/or the pharmaceutically acceptable salts thereof for the use in the treatment, including therapy and prophylaxis, of disease states such as inflammatory pain, asthma, angiogenesis, demyelating diseases of (a) the central nervous system, such as multiple sclerosis, transverse myelitis, optic neuritis, Devic's disease, and (b) the peripheral nervous system, such as Guillain-Barre syndrome or chronic inflammatory demyelinating polyneuropathy, as well as to the use of a compound of the formula I and/or the pharmaceutically acceptable salts thereof for the manufacture of a medicament for the treatment, including therapy and prophylaxis, of said disease states.

The compounds of the formula I and their pharmaceutically acceptable salts and their prodrugs can be administered to animals, preferably to mammals, and in particular to humans as pharmaceuticals for therapy or prophylaxis. They can be administered alone, or in mixtures with one another or in the form of pharmaceutical compositions, which permit enteral or parenteral administration.

The pharmaceutical compositions according to the invention can be administered orally, for example in the form of pills, tablets, lacquered tablets, coated tablets, granules, hard and soft gelatine capsules, solutions, syrups, emulsions, suspensions or aerosol mixtures. Administration can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical compositions according to the invention are prepared in a manner known per se and familiar to one skilled in the art, pharmaceutically acceptable inert inorganic and/or organic carrier substances and/or auxiliary substances being used in addition to one or more compounds of the formula I and/or their pharmaceutically acceptable salts and/or their prodrugs. For the production of pills, tablets, coated tablets and hard gelatine capsules it is possible to use, for example, lactose, corn starch or derivatives thereof, talc, stearic acid or its salts, etc. Carrier substances for soft gelatine capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0.5% to about 90% by weight of the compounds of the formula I and/or their pharmaceutically acceptable salts and/or their prodrugs. The amount of the active ingredient of the formula I and/or its pharmaceutically acceptable salts and/or its prodrugs in the pharmaceutical compositions normally is from about 0.5 mg to about 1000 mg, preferably from about 1 mg to about 500 mg.

In addition to the active ingredients of the formula I and/or their pharmaceutically acceptable salts and/or prodrugs and to carrier substances or excipients, the pharmaceutical compositions can contain auxiliary substances or additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their pharmaceutically acceptable salts and/or their prodrugs. In case a pharmaceutical composition contains two or more compounds of the formula I, the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a pharmaceutically acceptable salt and/or its prodrug, the pharmaceutical compositions can also contain one or more other pharmaceutically, therapeutically and/or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The compounds of the present invention are also useful as standard or reference compounds, for example as a quality standard or control, in tests or assays involving the inhibition of the LPA receptor LPAR5. Such compounds may be provided in a commercial kit, for example, for use in pharmaceutical research involving the LPA receptor LPAR5. For example, a compound of the present invention can be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention can be used to test their effectiveness.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or its salts can be used for diagnostic purposes, for example in in vitro diagnoses, and as an auxiliary in biochemical investigations. For example, a compound of the formula I can be used in an assay to identify the presence of the LPA receptor LPAR5 or to isolate the LPA receptor LPAR5 containing tissue in a substantially purified form. A compound of the invention can be labeled with, for example, a radioisotope, and the labeled compound bound to the LPA receptor LPAR5 is then detected using a routine method useful for detecting the particular label. Thus, a compound of the formula I or a salt thereof can be used as a probe to detect the location or amount of LPAR5 activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in detail in the examples given below which are intended to be merely illustrative of the present invention and not limiting it in either scope or spirit. Those with skill in the art will readily understand that known variations of the conditions and processes described in the examples can be used to synthesize the compounds of the present invention.

EXAMPLES

When in the final step of the synthesis of a compound an acid such as trifluoroacetic acid or acetic acid was used, for example when trifluoroacetic acid was employed to an acid-labile protecting group (for example a tBu group) or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt, formic acid salt or trifluoroacetic acid salt or hydrochloric acid salt. Likewise starting materials or intermediates bearing a basic center like, for example, a basic nitrogen were either obtained and used as free base or in salt form like, for example, a trifluoroacetic acid salt, a hydrobromic acid salt, a sulfuric acid salt, or a hydrochloric acid salt. Room temperature means a temperature of about 20° C. to 25° C.

Abbreviations
Acetonitrile MeCN
tert-Butyl tBu
Ethyl acetate EtOAc
Tetrahydrofuran THF
Trifluoroacetic acid TFA Example 1

6-Chloro-4,4-dicyclohexyl-4H-benzo[1,3]dioxine-2-carboxylic acid (Illustrative Example)

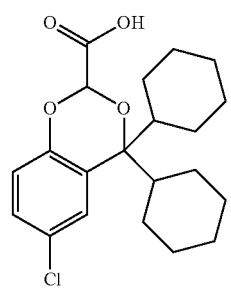 [SMILES: O=C(O)C1Oc2ccc(Cl)cc2C(C2CCCCC2)(C2CCCCC2)O1]

(i)
4-Chloro-2-(dicyclohexyl-hydroxy-methyl)-phenol

To a solution of 7.0 g of 5-Chloro-2-hydroxy-benzoic acid methyl ester in 38 ml of THF, 115.5 ml of a solution of cyclohexylmagnesium chloride in THF (2 M) was added slowly at room temperature. The reaction mixture was then heated to reflux for 5 h. After cooling to room temperature it was hydrolyzed with ice. Saturated aqueous $NH_4Cl$ was added until the white precipitate was dissolved. The aqueous phase was extracted with ether. The combined organic layers were dried over $MgSO_4$, filtered and concentrated under reduced pressure. The crude product was recrystallized from n-heptane to yield a bright yellow product. Yield: 5.2 g.

(ii) 6-Chloro-4,4-dicyclohexyl-4H-benzo[1,3]dioxine-2-carboxylic acid

To a suspension of 1.6 g of NaH (60% dispersion in mineral oil) and 131 mg of 18-crown-6 ether in 60 ml of anhydrous dioxane, a solution of 16.4 ml of a solution of dichloroacetic acid (1 M) in anhydrous dioxane was slowly added at room temperature. The reaction mixture was heated to 60° C. and a solution of 3.2 g of 4-Chloro-2-(dicyclohexyl-hydroxy-methyl)-phenol in 42 ml anhydrous dioxane was added and stirred at 90° C. for 6 h. After cooling to 0° C., the reaction mixture was quenched with 8 ml of isopropanol and poured on ice. The aqueous phase was extracted with ether, then acidified with HCl (2 M, to pH 1), and extracted with ethyl acetate. The combined organic layers were dried over $MgSO_4$, filtered and concentrated under reduced pressure. The crude product was recrystallized from n-heptane to yield a bright yellow product. Yield: 2.5 g.

MS (ES−): m/e=377.

Example 2

4,4-Dicyclohexyl-7-pyrrol-1-yl-4H-benzo[1,3]dioxine-2-carboxylic acid

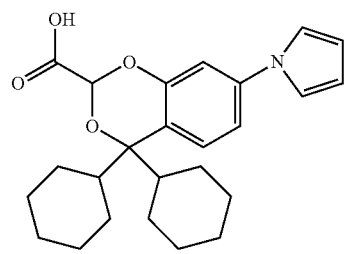 [SMILES: O=C(O)C1Oc2cc(-n3cccc3)ccc2C(C2CCCCC2)(C2CCCCC2)O1]

(i) 2-(Dicyclohexyl-hydroxy-methyl)-5-pyrrol-1-yl-phenol

To a solution of 217 mg of 2-Hydroxy-4-pyrrol-1-yl-benzoic acid methyl ester in 4 ml of THF, 2 ml of a solution of cyclohexylmagnesium chloride in THF (2 M) was added slowly at room temperature. The reaction mixture was then heated to reflux for 4 h. After cooling to room temperature it was hydrolized with ice. Saturated aqueous $NH_4Cl$ was added until the white precipitate was dissolved. The aqueous phase was extracted with ether. The combined organic layers were dried over $MgSO_4$, filtered and concentrated under reduced pressure. The crude product was used in the next reaction step. Yield: 504 mg.

(ii) 4,4-Dicyclohexyl-7-pyrrol-1-yl-4H-benzo[1,3]dioxine-2-carboxylic acid

To a suspension of 228 mg of NaH (60% dispersion in mineral oil) and 18 mg of 18-crown-6 ether in 8 ml of anhydrous dioxane, a solution of 2.3 ml of a solution of dichloroacetic acid (1 M) in anhydrous dioxane was slowly added at room temperature. The reaction mixture was heated to 60° C.

and a solution of 504 mg of 2-(Dicyclohexyl-hydroxy-methyl)-5-pyrrol-1-yl-phenol in 6 mL anhydrous dioxane was added and stirred at 95° C. for 6 h. After cooling to 0° C., the reaction mixture was quenched with 2 ml of isopropanol and poured on ice. The aqueous phase was extracted with ether, then acidified with HCl (2 M, to pH 1), and extracted with ethyl acetate. The combined organic layers were dried over $MgSO_4$, filtered and concentrated under reduced pressure. The residue was purified by preparative HPLC (C18 reverse phase column, elution with a water/MeCN gradient with 0.1% TFA). The fractions containing the product were evaporated and lyophilized to yield a white solid. Yield: 118 mg.

MS (ES−): m/e=408.

Example 3

4,4-Dicyclohexyl-6-methyl-4H-benzo[1,3]dioxine-2-carboxylic acid

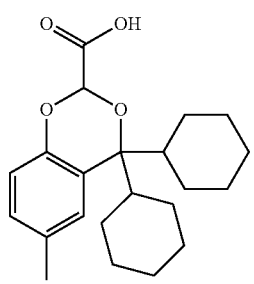 [SMILES: Cc1ccc2c(c1)C(C1CCCCC1)(C1CCCCC1)OC(C(=O)O)O2]

The title compound was prepared analogously as described in example 1.

MS (ES−): m/e=357.

Example 4

4,4-Dicyclohexyl-7-methoxy-4H-benzo[1,3]dioxine-2-carboxylic acid

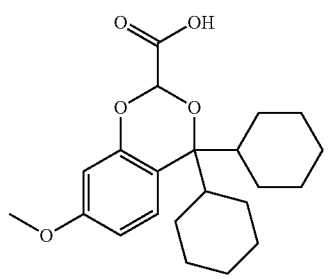 [SMILES: COc1ccc2c(c1)OC(C(=O)O)OC2(C1CCCCC1)C1CCCCC1]

The title compound was prepared analogously as described in example 1.

MS (ES−): m/e=373.

Example 5

4,4-Dicyclohexyl-6-fluoro-4H-benzo[1,3]dioxine-2-carboxylic acid

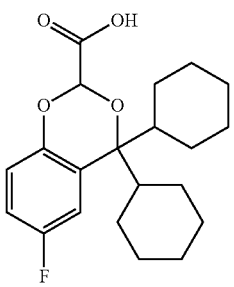 [SMILES: O=C(O)C1Oc2ccc(F)cc2C(C2CCCCC2)(C2CCCCC2)O1]

The title compound was prepared analogously as described in example 1.

MS (ES−): m/e=362.

Example 6

4,4-Dicyclohexyl-7-dimethylamino-4H-benzo[1,3]dioxine-2-carboxylic acid

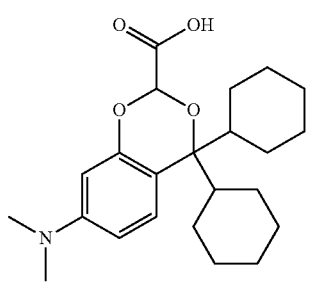 [SMILES: CN(C)c1ccc2c(c1)OC(C(=O)O)OC2(C1CCCCC1)C1CCCCC1]

The title compound was prepared analogously as described in example 1.

MS (ES−F): m/e=388.

Example 7

4,4-Dicyclohexyl-5,7-dimethoxy-4H-benzo[1,3]dioxine-2-carboxylic acid

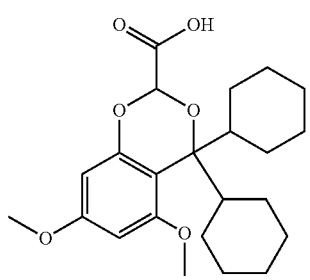 [SMILES: COc1cc(OC)c2c(c1)OC(C(=O)O)OC2(C1CCCCC1)C1CCCCC1]

The title compound was prepared analogously as described in example 1.

MS (ES−): m/e=403.

Example 8

4,4-Dicyclohexyl-4H-naphtho[2,3-d][1,3]dioxine-2-carboxylic acid

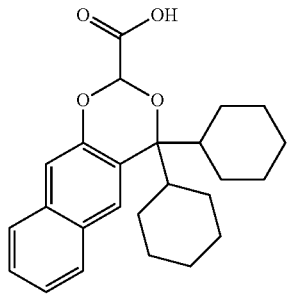 [SMILES: O=C(O)C1Oc2cc3ccccc3cc2C(C2CCCCC2)(C2CCCCC2)O1]

The title compound was prepared analogously as described in example 1.
MS (ES−): m/e=393.

Example 9

4,4-Dicyclohexyl-7-methyl-4H-benzo[1,3]dioxine-2-carboxylic acid

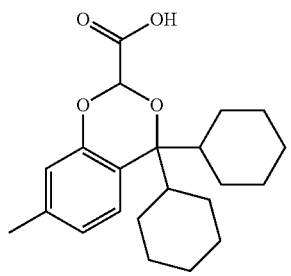 [SMILES: Cc1ccc2c(c1)OC(C(=O)O)OC2(C1CCCCC1)C1CCCCC1]

The title compound was prepared analogously as described in example 1.
MS (ES−): m/e=357.

Example 10

4,4-Dicyclohexyl-5-methyl-4H-benzo[1,3]dioxine-2-carboxylic acid

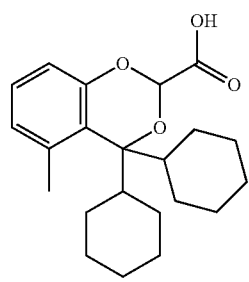 [SMILES: Cc1cccc2c1C(C1CCCCC1)(C1CCCCC1)OC(C(=O)O)O2]

The title compound was prepared analogously as described in example 1.
MS (ES−): m/e=357.

Example 11

7-Chloro-4,4-dicyclohexyl-4H-benzo[1,3]dioxine-2-carboxylic acid

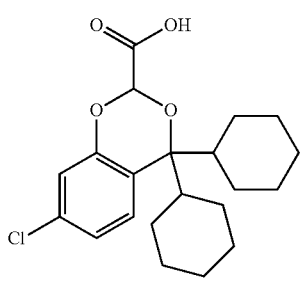 [SMILES: O=C(O)C1Oc2cc(Cl)ccc2C(C2CCCCC2)(C2CCCCC2)O1]

The title compound was prepared analogously as described in example 1.
MS (ES−): m/e=377.

Example 12

4,4-Dicyclohexyl-8-methyl-4H-benzo[1,3]dioxine-2-carboxylic acid

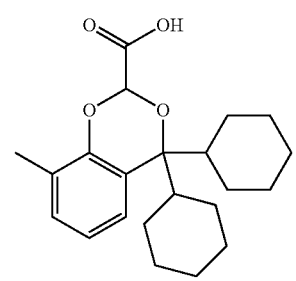 [SMILES: Cc1cccc2c1OC(C(=O)O)OC2(C1CCCCC1)C1CCCCC1]

The title compound was prepared analogously as described in example 1.
MS (ES−): m/e=357.

Example 13

4,4-Dicyclohexyl-8-fluoro-4H-benzo[1,3]dioxine-2-carboxylic acid

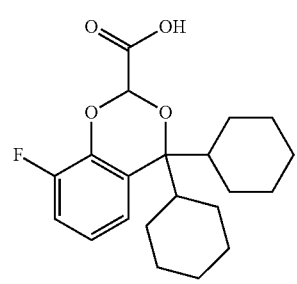 [SMILES: O=C(O)C1Oc2c(F)cccc2C(C2CCCCC2)(C2CCCCC2)O1]

The title compound was prepared analogously as described in example 1.
MS (ES−): m/e=361.

Example 14

6-tert-Butyl-4,4-dicyclohexyl-4H-benzo[1,3]dioxine-2-carboxylic acid

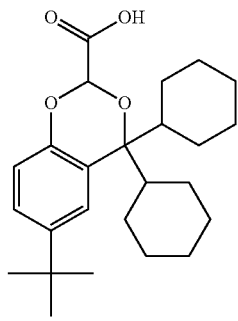 [SMILES: CC(C)(C)c1ccc2c(c1)C(C1CCCCC1)(C1CCCCC1)OC(C(=O)O)O2]

The title compound was prepared analogously as described in example 1.

MS (ES−): m/e=399.

Example 15

4,4-Dicyclohexyl-6-iodo-4H-benzo[1,3]dioxine-2-carboxylic acid

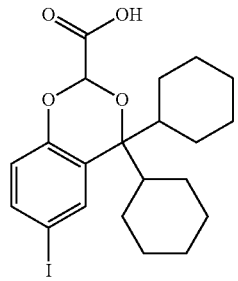 [SMILES: O=C(O)C1Oc2ccc(I)cc2C(C2CCCCC2)(C2CCCCC2)O1]

The title compound was prepared analogously as described in example 1.

MS (ES−): m/e=469.

Example 16

4,4-Dicyclohexyl-6-trifluoromethyl-4H-benzo[1,3]dioxine-2-carboxylic acid

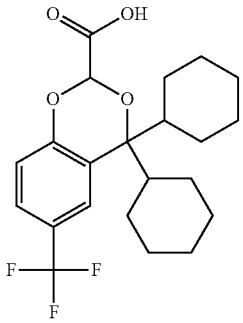 [SMILES: O=C(O)C1Oc2ccc(C(F)(F)F)cc2C(C2CCCCC2)(C2CCCCC2)O1]

The title compound was prepared analogously as described in example 1.

MS (ES−): m/e=411.

Example 17

6-Chloro-4,4-dicyclohexyl-2-methyl-4H-benzo[1,3]dioxine-2-carboxylic acid

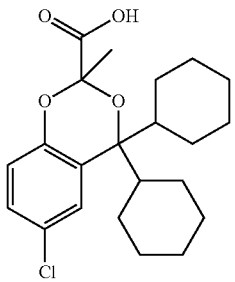 [SMILES: CC1(C(=O)O)Oc2ccc(Cl)cc2C(C2CCCCC2)(C2CCCCC2)O1]

The title compound was prepared analogously as described in example 1.

MS (ES−): m/e=391.

Example 18

4,4-Dicyclohexyl-6-trifluoromethoxy-4H-benzo[1,3]dioxine-2-carboxylic acid

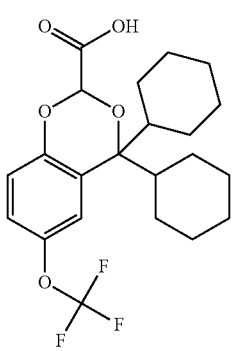 [SMILES: O=C(O)C1Oc2ccc(OC(F)(F)F)cc2C(C2CCCCC2)(C2CCCCC2)O1]

The title compound was prepared analogously as described in example 1.

MS (ES−): m/e=427.

Example 19

6-Chloro-4,4-dicyclohexyl-7-fluoro-4H-benzo[1,3]dioxine-2-carboxylic acid

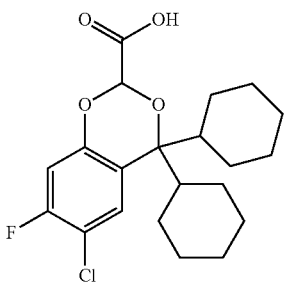 [SMILES: O=C(O)C1Oc2cc(F)c(Cl)cc2C(C2CCCCC2)(C2CCCCC2)O1]

The title compound was prepared analogously as described in example 1.

MS (ES−): m/e=395.

Example 20

6-Chloro-4,4-dicyclohexyl-8-fluoro-4H-benzo[1,3]dioxine-2-carboxylic acid

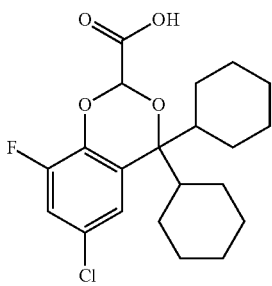 [SMILES: O=C(O)C1Oc2c(F)cc(Cl)cc2C(C2CCCCC2)(C2CCCCC2)O1]

The title compound was prepared analogously as described in example 1.
MS (ES−): m/e=395.

Example 21

6-Chloro-4,4-dicyclohexyl-5-fluoro-4H-benzo[1,3]dioxine-2-carboxylic acid

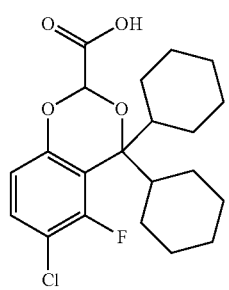 [SMILES: O=C(O)C1Oc2ccc(Cl)c(F)c2C(C2CCCCC2)(C2CCCCC2)O1]

The title compound was prepared analogously as described in example 1.
MS (ES−): m/e=395.

Example 22

6-(4-Chloro-phenoxy)-4,4-dicyclohexyl-4H-benzo[1,3]dioxine-2-carboxylic acid

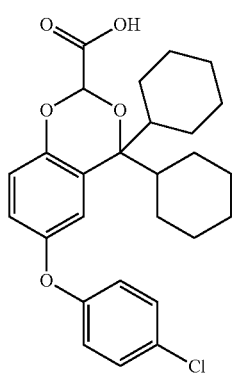 [SMILES: O=C(O)C1Oc2ccc(Oc3ccc(Cl)cc3)cc2C(C2CCCCC2)(C2CCCCC2)O1]

The title compound was prepared analogously as described in example 1.
MS (ES−): m/e=469.

Example 23

4,4-Dicyclohexyl-6-pyridin-4-yl-4H-benzo[1,3]dioxine-2-carboxylic acid

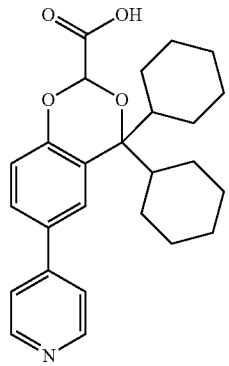 [SMILES: O=C(O)C1Oc2ccc(-c3ccncc3)cc2C(C2CCCCC2)(C2CCCCC2)O1]

The title compound was prepared analogously as described in example 1.
MS (ES+): m/e=422.

Example 24

4,4-Dicyclohexyl-6-(3-methoxy-phenoxy)-4H-benzo[1,3]dioxine-2-carboxylic acid

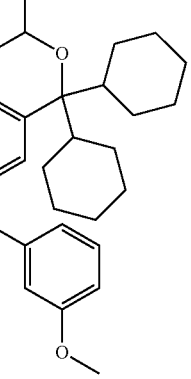

The title compound was prepared analogously as described in example 1.
MS (ES−): m/e=465.

Example 25

6-(3-Chloro-phenoxy)-4,4-dicyclohexyl-4H-benzo[1,3]dioxine-2-carboxylic acid

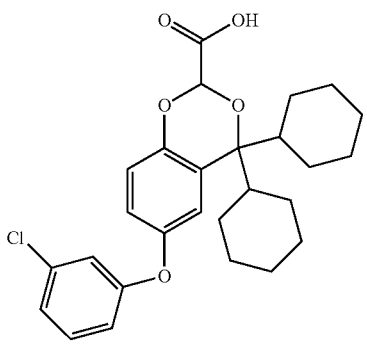 [SMILES: O=C(O)C1Oc2ccc(Oc3cccc(Cl)c3)cc2C(C2CCCCC2)(C2CCCCC2)O1]

The title compound was prepared analogously as described in example 1.
MS (ES−): m/e=469.

Example 26

6-(4-Chloro-benzoyl)-4,4-dicyclohexyl-4H-benzo[1,3]dioxine-2-carboxylic acid

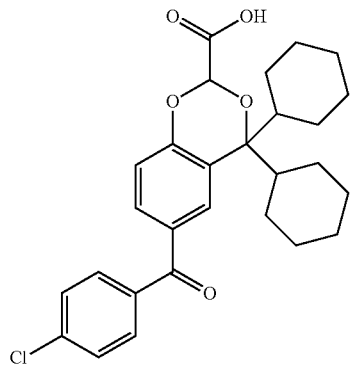 [SMILES: O=C(c1ccc(Cl)cc1)c1ccc2c(c1)C(C1CCCCC1)(C1CCCCC1)OC(C(=O)O)O2]

The title compound was prepared analogously as described in example 1.
MS (ES−): m/e=483.

Example 27

4,4-Dicyclohexyl-6-(pyridin-3-yloxy)-4H-benzo[1,3]dioxine-2-carboxylic acid

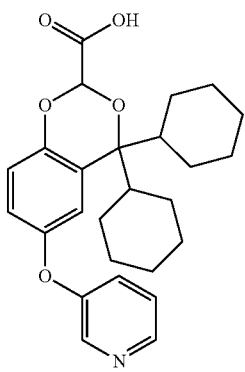 [SMILES: O=C(O)C1Oc2ccc(Oc3cccnc3)cc2C(C2CCCCC2)(C2CCCCC2)O1]

The title compound was prepared analogously as described in example 1.
MS (ES+): m/e=438.

Example 28

4,4-Dicyclohexyl-4H-benzo[1,3]dioxine-2-carboxylic acid

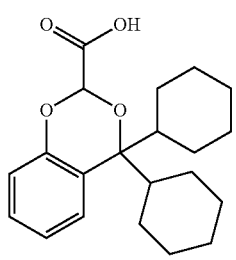 [SMILES: O=C(O)C1Oc2ccccc2C(C2CCCCC2)(C2CCCCC2)O1]

The title compound was prepared analogously as described in example 1.
MS (ES−): m/e=348.

Example 29

4,4-Dicyclohexyl-8-methoxy-4H-benzo[1,3]dioxine-2-carboxylic acid

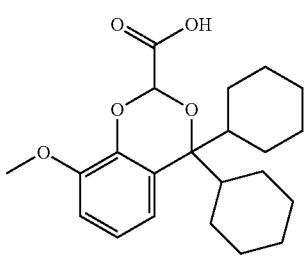 [SMILES: COc1cccc2c1OC(C(=O)O)OC2(C1CCCCC1)C1CCCCC1]

The title compound was prepared analogously as described in example 1.
MS (ES−): m/e=373.

Example 30

4,4-Dicyclohexyl-5-ethoxy-4H-benzo[1,3]dioxine-2-carboxylic acid

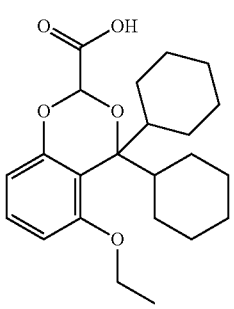 [SMILES: CCOc1cccc2c1C(C1CCCCC1)(C1CCCCC1)OC(C(=O)O)O2]

The title compound was prepared analogously as described in example 1.
MS (ES−): m/e=387.

Example 31

7-Butoxy-4,4-dicyclohexyl-4H-benzo[1,3]dioxine-2-carboxylic acid

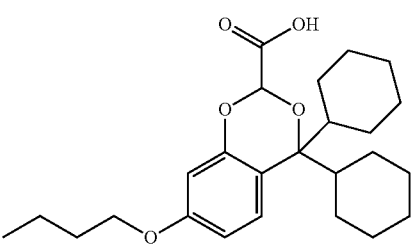 [SMILES: CCCCOc1ccc2c(c1)OC(C(=O)O)OC2(C1CCCCC1)C1CCCCC1]

The title compound was prepared analogously as described in example 1.
MS (ES−): m/e=415.

Example 32

6,8-Dichloro-4,4-dicyclohexyl-4H-benzo[1,3]dioxine-2-carboxylic acid

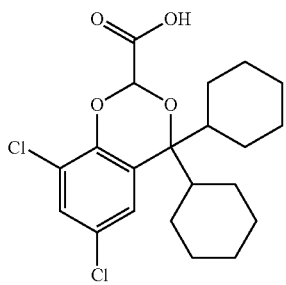 [SMILES: O=C(O)C1Oc2c(Cl)cc(Cl)cc2C(C2CCCCC2)(C2CCCCC2)O1]

The title compound was prepared analogously as described in example 1.
MS (ES−): m/e=411.

Example 33

1,1-Dicyclohexyl-1H-naphtho[2,1-d][1,3]dioxine-3-carboxylic acid

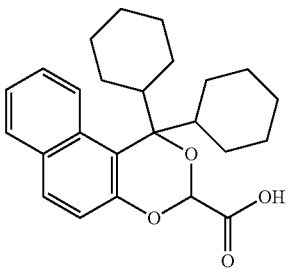 [SMILES: O=C(O)C1Oc2ccc3ccccc3c2C(C2CCCCC2)(C2CCCCC2)O1]

The title compound was prepared analogously as described in example 1.
MS (ES−): m/e=393.

Example 34

4,4-Dicyclohexyl-6-methoxy-4H-benzo[1,3]dioxine-2-carboxylic acid

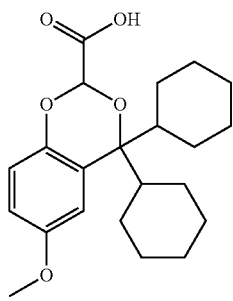 [SMILES: COc1ccc2c(c1)C(C1CCCCC1)(C1CCCCC1)OC(C(=O)O)O2]

The title compound was prepared analogously as described in example 1.
MS (ES−): m/e=373.

Example 35

4,4-Dicyclohexyl-6-phenyl-4H-benzo[1,3]dioxine-2-carboxylic acid

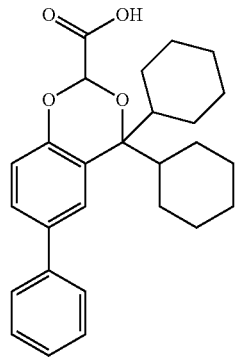 [SMILES: O=C(O)C1Oc2ccc(-c3ccccc3)cc2C(C2CCCCC2)(C2CCCCC2)O1]

The title compound was prepared analogously as described in example 1.
MS (ES−): m/e=419.

Example 36

4,4-Dicyclohexyl-7-methoxy-5-methyl-4H-benzo[1,3]dioxine-2-carboxylic acid

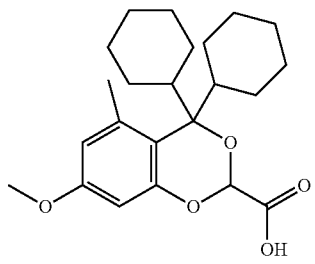 [SMILES: COc1cc(C)c2c(c1)OC(C(=O)O)OC2(C1CCCCC1)C1CCCCC1]

The title compound was prepared analogously as described in example 1.
MS (ES−): m/e=387.

Example 37

7-Benzyloxy-4,4-dicyclohexyl-4H-benzo[1,3]dioxine-2-carboxylic acid

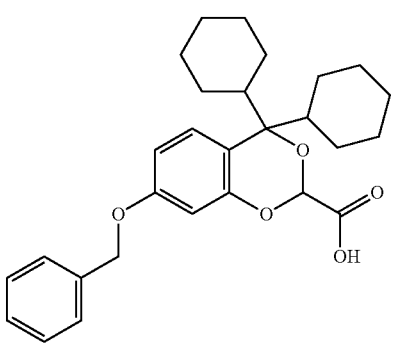 [SMILES: O=C(O)C1Oc2cc(OCc3ccccc3)ccc2C(C2CCCCC2)(C2CCCCC2)O1]

The title compound was prepared analogously as described in example 1.
MS (ES−): m/e=449.

Example 38

6-Chloro-4,4-dicyclohexyl-7-methoxy-4H-benzo[1,3]dioxine-2-carboxylic acid

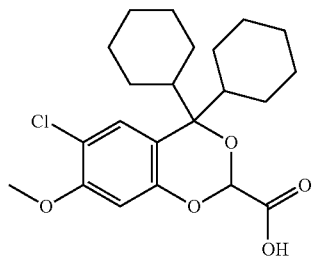 [SMILES: COc1cc2c(cc1Cl)C(C1CCCCC1)(C1CCCCC1)OC(C(=O)O)O2]

The title compound was prepared analogously as described in example 1.
MS (ES−): m/e=407.

Example 39

4,4-Dicyclohexyl-6-(pyrrolidine-1-sulfonyl)-4H-benzo[1,3]dioxine-2-carboxylic acid

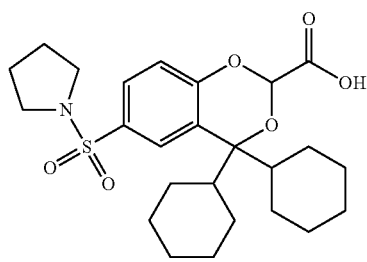 [SMILES: O=C(O)C1Oc2ccc(S(=O)(=O)N3CCCC3)cc2C(C2CCCCC2)(C2CCCCC2)O1]

The title compound was prepared analogously as described in example 1.
MS (ES+): m/e=478.

Example 40

4,4-Dicyclohexyl-7-morpholin-4-yl-4H-benzo[1,3]dioxine-2-carboxylic acid

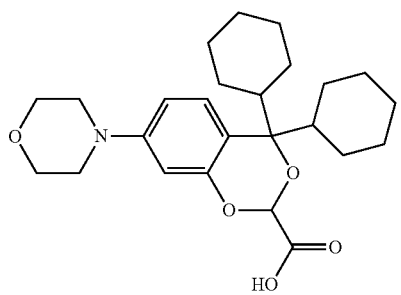 [SMILES: O=C(O)C1Oc2cc(N3CCOCC3)ccc2C(C2CCCCC2)(C2CCCCC2)O1]

The title compound was prepared analogously as described in example 1.
MS (ES-F): m/e=430.

Example 41

4,4-Dicyclohexyl-4H-naphtho[1,2-d][1,3]dioxine-2-carboxylic acid

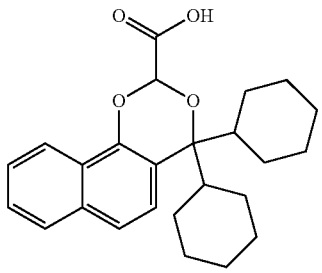 [SMILES: O=C(O)C1Oc2c(ccc3ccccc23)C(C2CCCCC2)(C2CCCCC2)O1]

The title compound was prepared analogously as described in example 1.
MS (ES−): m/e=393.

Example 42

6-Chloro-4,4-dicyclohexyl-8-methyl-4H-benzo[1,3]dioxine-2-carboxylic acid

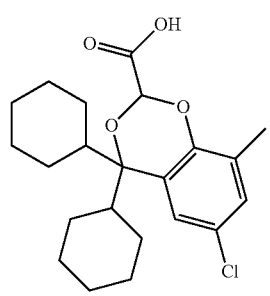 [SMILES: Cc1cc(Cl)cc2c1OC(C(=O)O)OC2(C1CCCCC1)C1CCCCC1]

The title compound was prepared analogously as described in example 1.
MS (ES−): m/e=391.

Example 43

6-Chloro-4,4-dicyclohexyl-7-methyl-4H-benzo[1,3]dioxine-2-carboxylic acid

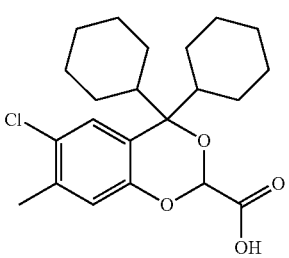 [SMILES: Cc1cc2c(cc1Cl)C(C1CCCCC1)(C1CCCCC1)OC(C(=O)O)O2]

The title compound was prepared analogously as described in example 1.
MS (ES−): m/e=391.

Example 44

4,4-Dicyclohexyl-5,7-difluoro-4H-benzo[1,3]dioxine-2-carboxylic acid

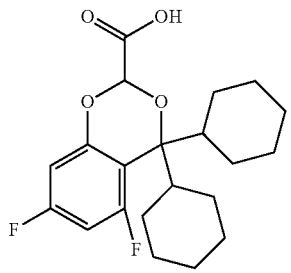 [SMILES: O=C(O)C1Oc2cc(F)cc(F)c2C(C2CCCCC2)(C2CCCCC2)O1]

The title compound was prepared analogously as described in example 1.
MS (ES−): m/e=379.

Example 45

1,1-Dicyclohexyl-7,8,9,10-tetrahydro-1H-naphtho[2,1-d][1,3]dioxine-3-carboxylic acid

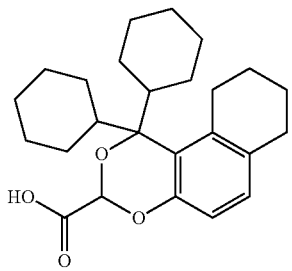 [SMILES: O=C(O)C1Oc2ccc3c(c2C(C2CCCCC2)(C2CCCCC2)O1)CCCC3]

The title compound was prepared analogously as described in example 1.
MS (ES−): m/e=397.

Example 46

4,4-Dicyclohexyl-8-trifluoromethoxy-4H-benzo[1,3]dioxine-2-carboxylic acid

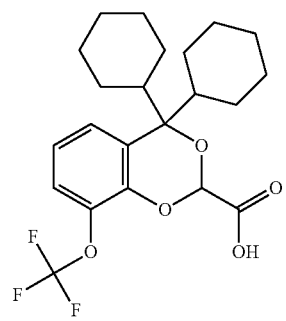 [SMILES: O=C(O)C1Oc2c(OC(F)(F)F)cccc2C(C2CCCCC2)(C2CCCCC2)O1]

The title compound was prepared analogously as described in example 1.
MS (ES−): m/e=427.

Example 47

8-tert-Butyl-4,4-dicyclohexyl-4H-benzo[1,3]dioxine-2-carboxylic acid

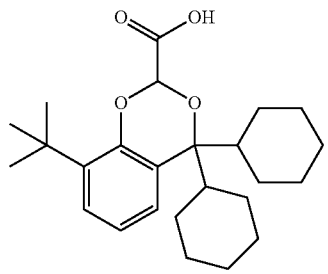 [SMILES: CC(C)(C)c1cccc2c1OC(C(=O)O)OC2(C1CCCCC1)C1CCCCC1]

The title compound was prepared analogously as described in example 1.
MS (ES−): m/e=399.

Example 48

10-Benzyl-4,4-dicyclohexyl-4H-naphtho[2,3-d][1,3]dioxine-2-carboxylic acid

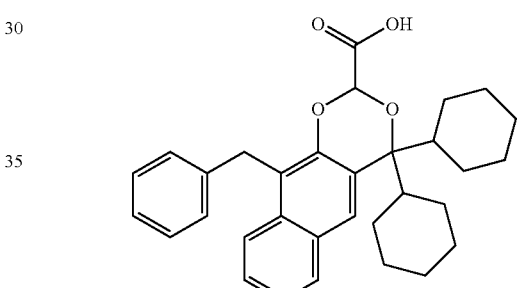

The title compound was prepared analogously as described in example 1.
MS (ES−): m/e=483.

Example 49

4,4-Dicyclohexyl-7-diethylamino-4H-benzo[1,3]dioxine-2-carboxylic acid

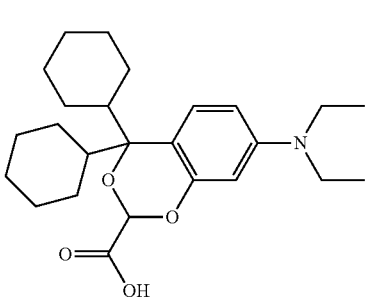 [SMILES: CCN(CC)c1ccc2c(c1)OC(C(=O)O)OC2(C1CCCCC1)C1CCCCC1]

The title compound was prepared analogously as described in example 1.
MS (ES−F): m/e=416.

Example 50

6-Bromo-4,4-dicyclohexyl-4H-benzo[1,3]dioxine-2-carboxylic acid

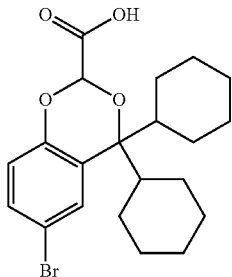

The title compound was prepared analogously as described in example 1.
MS (ES−): m/e=421.

Example 51

6-Chloro-4,4-dicyclopentyl-4H-benzo[1,3]dioxine-2-carboxylic acid

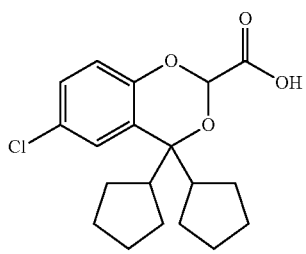 [SMILES: O=C(O)C1Oc2ccc(Cl)cc2C(C2CCCC2)(C2CCCC2)O1]

The title compound was prepared analogously as described in example 1.
MS (ES−): m/e=349.

Example 52

6-Chloro-4-cycloheptyl-4H-benzo[1,3]dioxine-2-carboxylic acid

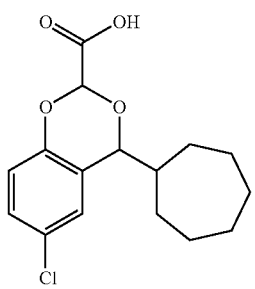 [SMILES: O=C(O)C1Oc2ccc(Cl)cc2C(C2CCCCCC2)O1]

The title compound was prepared analogously as described in example 1 by using 5-Chloro-2-hydroxy-benzaldehyde and cycloheptylmagnesium chloride instead of 5-Chloro-2-hydroxy-benzoic acid methyl ester and cyclohexylmagnesium chloride in step (i).
MS (ES−): m/e=309.

Example 53

6-Chloro-4-cyclohexyl-4-phenyl-4H-benzo[1,3]dioxine-2-carboxylic acid (Illustrative Example)

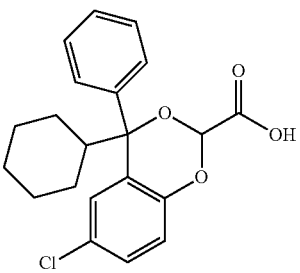 [SMILES: O=C(O)C1Oc2ccc(Cl)cc2C(c2ccccc2)(C2CCCCC2)O1]

The title compound was prepared analogously as described in example 1.
MS (ES−): m/e=371.

Example 54

6-Bromo-4,4-dicyclohexyl-4H-benzo[1,3]dioxine-2-carboxylic acid

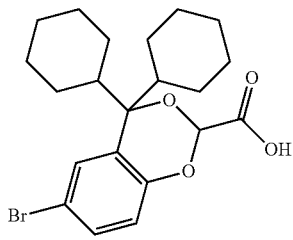 [SMILES: O=C(O)C1Oc2ccc(Br)cc2C(C2CCCCC2)(C2CCCCC2)O1]

The title compound was prepared analogously as described in example 1.
MS (ES−): m/e=421.

Example 55

6-Chloro-4,4-dicycloheptyl-4H-benzo[1,3]dioxine-2-carboxylic acid

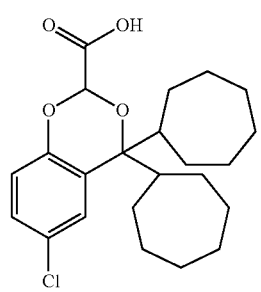 [SMILES: O=C(O)C1Oc2ccc(Cl)cc2C(C2CCCCCC2)(C2CCCCCC2)O1]

The title compound was prepared analogously as described in example 1.
MS (ES−): m/e=405.

Example 56

6-Chloro-4,4-dicyclooctyl-4H-benzo[1,3]dioxine-2-carboxylic acid

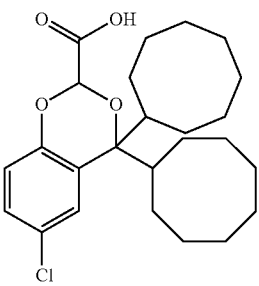 [SMILES: O=C(O)C1Oc2ccc(Cl)cc2C(C2CCCCCCC2)(C2CCCCCCC2)O1]

The title compound was prepared analogously as described in example 1.
MS (ES−): m/e=433.

Example 57

6-Chloro-4,4-dicycloheptyl-7-methyl-4H-benzo[1,3]dioxine-2-carboxylic acid

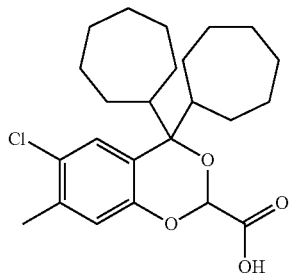 [SMILES: Cc1cc2c(cc1Cl)C(C1CCCCCC1)(C1CCCCCC1)OC(C(=O)O)O2]

The title compound was prepared analogously as described in example 1.
MS (ES−): m/e=419.

Example 58

4,4-Dicycloheptyl-6-trifluoromethoxy-4H-benzo[1,3]dioxine-2-carboxylic acid

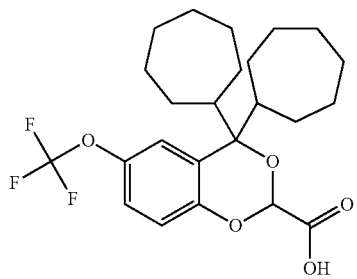 [SMILES: O=C(O)C1Oc2ccc(OC(F)(F)F)cc2C(C2CCCCCC2)(C2CCCCCC2)O1]

The title compound was prepared analogously as described in example 1.
MS (ES−): m/e=455.

Example 59

6-Bromo-4,4-dicycloheptyl-4H-benzo[1,3]dioxine-2-carboxylic acid

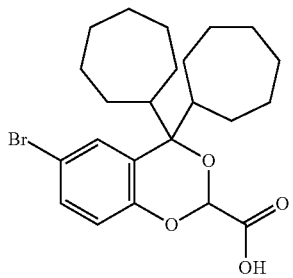 [SMILES: O=C(O)C1Oc2ccc(Br)cc2C(C2CCCCCC2)(C2CCCCCC2)O1]

The title compound was prepared analogously as described in example 1.
MS (ES−): m/e=449.

Example 60

5-(6-Chloro-4,4-dicyclohexyl-4H-benzo[1,3]dioxin-2-yl)-1H-tetrazole

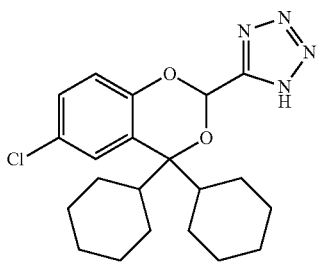 [SMILES: Clc1ccc2c(c1)C(C1CCCCC1)(C1CCCCC1)OC(c1nnn[nH]1)O2]

(i) 6-Chloro-4,4-dicyclohexyl-4H-benzo[1,3]dioxine-2-carboxylic amide

A solution of 4.8 g 6-chloro-4,4-dicyclohexyl-4H-benzo[1,3]dioxine-2-carboxylic acid and 2.44 g 1,1'-carbonyl diimidazole in 122 ml THF was stirred for 2 h at room temperature. Then 122 ml 25% aqueous $NH_4OH$ was added and the reaction mixture stirred for 16 h at room temperature. The precipitate was filtered, washed with cold water and dried over $P_2O_5$. Recrystallization from EtOAc yielded the desired product. Yield: 3.55 g.

(ii) 6-Chloro-4,4-dicyclohexyl-4H-benzo[1,3]dioxine-2-carbonitrile 4.19 ml Trifluoroacetic anhydride is added dropwise to a solution of 3.25 g 6-chloro-4,4-dicyclohexyl-4H-benzo[1,3]dioxine-2-carboxylic amide and 1.7 ml pyridine in 29 ml dioxane at 0° C. The reaction was stirred for 30 min at 0° C. and for 4 h at room temperature. The reaction mixture was then poured on ice water and stirred for 30 min. The precipitate was filtered, washed with water and dried over $P_2O_5$ under vaccum. Yield: 2.95 g.

(iii) 5-(6-Chloro-4,4-dicyclohexyl-4H-benzo[1,3]dioxin-2-yl)-1H-tetrazole 500 mg 6-chloro-4,4-dicyclohexyl-4H-benzo[1,3]dioxine-2-carbonitrile and 572 mg trimethyltin azide were dissolved in 23 ml xylene. The reaction mixture was refluxed for 4 hours. Then the solvent was removed in vacuo and the crude product purified by preparative HPLC (C18 reverse phase column, elution with water/MeCN gradient with 0.1% TFA). The fractions containing the product were evaporated and lyophilized to yield a solid which was washed three times with heptanes to remove traces of tin by-product. Yield: 238 mg.

MS (ES+): m/e=444 (M+H$^+$+MeCN).

Example 61

3-(6-Chloro-4,4-dicyclohexyl-4H-benzo[1,3]dioxin-2-yl)-4H-[1,2,4]oxadiazol-5-one

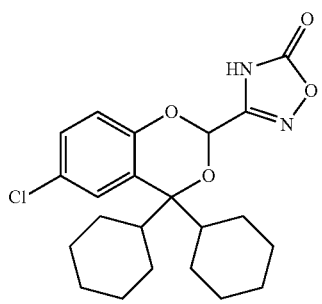 [SMILES: O=c1[nH]c(C2Oc3ccc(Cl)cc3C(C3CCCCC3)(C3CCCCC3)O2)no1]

(i) N-Hydroxy-6-chloro-4,4-dicyclohexyl-4H-benzo[1,3]dioxine-2-carboxamidine A solution of 500 mg 6-chloro-4,4-dicyclohexyl-4H-benzo[1,3]dioxine-2-carbonitrile, 204 mg hydroxylamine hydrochloride and 0.41 ml triethylamine in 7 ml methanol was refluxed for 8 hours. The solvent was removed in vacuo, the residue dissolved in EtOAc and washed with water. The aqueous phase was extracted with EtOAc, the combined organic phases were washed with brine and dried over MgSO4. After removal of the solvent, the crude product was directly used in the next step. Yield: 540 mg.

(ii) 3-(6-Chloro-4,4-dicyclohexyl-4H-benzo[1,3]dioxin-2-yl)-4H-[1,2,4]oxadiazol-5-one To a solution of 500 mg N-hydroxy-6-chloro-4,4-dicyclohexyl-4H-benzo[1,3]dioxine-2-carboxamidine in 3.7 ml ethanol was added 0.7 ml of a sodium methoxide solution (30% in methanol) and then 0.617 ml diethyl carbonate. The mixture was refluxed for 2 h. After cooling to room temperature, the solvent was removed in vacuo. The residue was dissolved in 3.4 ml water and 1M aqueous HCl was added until pH7 was reached. The obtained precipitate was filtered, washed with water, dissolved in EtOAc and dried with MgSO$_4$. Then the solvent was removed in vacuo and the crude product purified by preparative HPLC (C18 reverse phase column, elution with water/MeCN gradient with 0.1% TFA). The fractions containing the product were evaporated and lyophilized to yield a solid. Yield: 257 mg.

MS (ESI−): m/e=417.

Example 62

6-Chloro-4,4-dicyclohexyl-4H-benzo[1,3]dioxine-2-carboxylic acid methyl ester

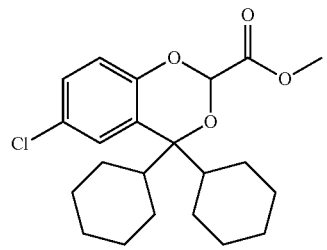 [SMILES: COC(=O)C1Oc2ccc(Cl)cc2C(C2CCCCC2)(C2CCCCC2)O1]

A solution of 2 g 6-chloro-4,4-dicyclohexyl-4H-benzo[1,3]dioxine-2-carboxylic acid and 73 mg para-toluenesulfonic acid in 4 ml methanol was refluxed for 4 hours. After cooling to room temperature, 50 mg sodium bicarbonate was added and the solvent was removed in vacuo. The residue was dissolved in 10 ml EtOAc, washed with water and dried over Na$_2$SO$_4$. The solvent was removed in vacuo. Yield 1.3 g.

$^1$H-NMR (500 MHz, D$_6$-dimethyl sulfoxide): δ (ppm)= 7.30 (1H, dxd, J=8.5 Hz, 2.5 Hz), 7.25 (1H, d, J=2.5 Hz), 7.04 (1H, d, J=8.5 Hz), 5.26 (1H, s), 3.80 (3H, s), 2.22-2.14 (1H, m), 1.87-1.61 (8H, m), 1.58-1.48 (2H, m), 1.45-1.39 (1H, m), 1.37-1.04 (7H, m), 0.87-0.71 (2H, m), 0.03-0.07 ppm (1H, m).

Example 63

5-(6-Chloro-4,4-dicyclohexyl-4H-benzo[1,3]dioxin-2-yl)-3H-[1,3,4]oxadiazol-2-one

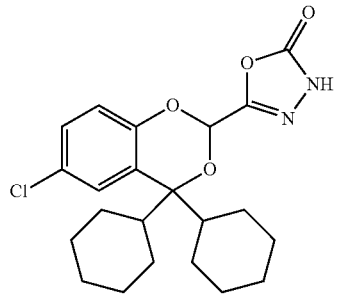 [SMILES: O=c1[nH]nc(C2Oc3ccc(Cl)cc3C(C3CCCCC3)(C3CCCCC3)O2)o1]

(i) 6-Chloro-4,4-dicyclohexyl-4H-benzo[1,3]dioxine-2-carboxylic acid hydrazide A solution of 2.47 g 6-chloro-4,4-dicyclohexyl-4H-benzo[1,3]dioxine-2-carboxylic acid methyl ester in 9 ml ethanol was added to a solution of 0.61 ml hydrazine monohydrate in 9 ml ethanol. The reaction mixture was refluxed for 1 h. After cooling to room temperature, the solvent was removed in vacuo. The crude product was purified by preparative HPLC (C18 reverse phase column, elution with water/TFA gradient with 0.1% TFA). The fractions containing the product were evaporated and lyophilized to yield a solid. Yield: 1.1 g.

(ii) 5-(6-Chloro-4,4-dicyclohexyl-4H-benzo[1,3]dioxin-2-yl)-3H-[1,3,4]oxadiazol-2-one To a solution of 300 mg 6-chloro-4,4-dicyclohexyl-4H-benzo[1,3]dioxine-2-carboxylic acid hydrazide in 4.3 ml toluene was added 4 ml of a 1.9M solution of phosgene in toluene. The reaction mixture was heated to reflux for 4 h. After cooling to room temperature, the reaction mixture was diluted with EtOAc, washed with water and brine and dried with MgSO$_4$. Then the solvent was removed in vacuo and the crude product purified by preparative HPLC (C18 reverse phase column, elution with water/MeCN gradient with 0.1% TFA). The fractions containing the product were evaporated and lyophilized to yield a solid. Yield: 180 mg.

MS (ES+): m/e=419.

Pharmacological Testing

The ability of the compounds of the formula I to inhibit or bind the LPA receptor LPAR5 can be assessed by determining the effect on cellular function. This ability of such compounds was evaluated in a platelet aggregation assay such as the Born method using single cuvettes and for mast cells and microglia cells with the Fluorometric Imaging Plate Reader (FLIPR) assay by Molecular Devices Inc.

A) Aggregation Assay for Washed Human Blood Platelets (Thrombocytes)

Whole blood was collected from healthy volunteers using 3×20 ml syringes containing each 1/10 volume of buffered citrate. The anticoagulated whole blood was transferred into 50 ml polypropylene conical tubes (30 ml per tube). The tubes were centrifuged for 10 minutes at 150×g at room temperature without using the centrifuge brake. This procedure results in a lower phase of cellular components and a supernatant (upper phase) of platelet rich plasma (PRP). The PRP phase was collected from each tube and pooled for each donor. To avoid carry over of cellular components following first centrifugation, approximately 5 ml of PRP was left in the tube. The platelet concentration was determined using a ABX Micros 60 counter. The PRP phase was transferred to a new 50 ml tube. After 10 minutes standing at room temperature, 1 µl PGI$_2$ (1 mM in Tris-HCl/pH 8.8) and 180 µl ACD/A were added per ml PRP. The PRP was then transferred to new 10 ml tube and centrifuged for 10 minutes at 500×g. After centrifugation a cellular pellet is visible at the bottom of the tube. The supernatant was carefully discarded and the cellular pellet, consisting of human blood platelets was then dissolved in 10 ml buffer T (buffer T composition: 145 mM NaCl, 5 mM KCl, 0.1 mM MgCl$_2$×6 H$_2$O, 15 mM HEPES, 5.5 mM glucose, pH 7.4). Platelet concentration in this solution was determined and buffer T was added to obtain a final concentration of 3.5×10$^5$ platelets per ml.

After 10 minutes at room temperature, 1 µl PGI$_2$ per ml platelet solution was added and distributed into new 10 ml tubes. After a centrifugation step, 10 minutes at 500×g, supernatant was discarded and the platelets were resuspended in buffer T to a final concentration of 3.5×10$^5$ platelets per ml buffer T. Before use, platelet-containing buffer equilibrated for 30 minutes at room temperature. The human platelet aggregation assay was performed in single use cuvettes using the Platelet Aggregation Profiler® (PAP-4 or -8E, BIO/DATA Corporation). For a single experiment, 320 µl of platelet solution were transferred into an assay cuvette, 20 µl of calcium citrate solution (10 mM in H$_2$O) and 20 µl of fibrinogen solution (20 mg/ml H$_2$O) were added. The aggregation assay was performed in the assay cuvette at 37° C. and with 1.200 rpm stirring. To determine the EC$_{50}$, eight assay cuvettes were loaded as described above with different concentrations of LPA. Aggregation was measured over 6 minutes at 37° C. with 1200 rpm (revolutions per minute) stirring. Results of the assay are expressed as % activation, and are calculated using maximum aggregation (T$_{max}$) or area under curve (AUC) of the absorbance over 6 minutes. The inhibitory effect (IC$_{50}$) of the test compounds was determined as the reduction of the maximal aggregation. Test compound was added prior starting the experiment with an incubation time of the test compound of 5 minutes at 37° C. with 1200 rpm stirring. The IC$_{50}$ data of the above described platelet aggregation assay using human washed platelets for exemplary compounds of the present invention are shown in Table 1.

TABLE 1

| Example | IC$_{50}$ (µM) |
|---------|----------------|
| 1       | 1.1            |
| 30      | 5.9            |
| 36      | 2.4            |
| 37      | 11.3           |
| 46      | 5.4            |
| 49      | 2.7            |

B) Use of the Fluorometric Imaging Plate Reader (FLIPR) Assay for the Determination of Intracellular Ca$^{2+}$ Release in Human Mast Cell Line HMC-1 and the Murine Microglia Cell Line BV-2

The ability of the compounds of the formula I to inhibit or bind the LPA receptor LPAR5 can be assessed by determining the intracellular Ca$^{2+}$ release in human or animal cells. For the analysis of activating potential of LPA and the inhibitory effects of compounds of the formula I two cell lines were used with high LPAR5 expression, the human mast cell line HMC-1 and the murine microglia cell line BV-2 (Figures 1 and 2). For the FLIPR assay using human mast cells in a 96-well-format, HMC-1 suspension cells from flask culture were harvested, resuspended and counted. 14×10$^6$ HMC-1 cells were transferred into a new 50 ml tube, centrifuged for 3 minutes at 540×g. The resulting cell pellet at the bottom of the tube was resuspended with 15 ml loading buffer (loading buffer contained HBSS buffer (pH 7.4), 0.1% BSA (bovine serum albumin), 2 µM FLUO-4 dye; HBSS buffer (pH 7.4) contained 1×HBSS, 20 mM HEPES, 0.01% Pluronic F-127, 2.5 mM Probenicid).

Cells in loading buffer were incubated for 45-60 minutes at 37° C. After incubation cells were centrifuged for 3 minutes at 540×g and resuspended with 21 ml of HBSS buffer (pH 7.4). Each well of a poly-D-lysine coated 96-well-plate was filled with 150 µl cell solution, an equivalent of 100 000 cells/well. The 96-well-plate was centrifuged for 2 minutes at 100×g (without brake) prior a recovery time of 30 minutes at 37° C. After this procedure cells were stimulated with LPA (in HBSS pH 7.4 and 0.1% BSA) to determine the EC$_{50}$ of LPA in HMC-1 cells. For the determination of the inhibitory effect of compounds of the formula I, test compounds were added to the cells in the 96-well-plate 10 minutes prior the addition of LPA. Results of the assay are expressed as % activation, and are calculated using maximum peak of activation (A$_{max}$). The IC$_{50}$ data of the above described FLIPR assay using human mast cell line HMC-1 for exemplary compounds of the present invention are shown in Table 2. Adherent BV-2 cells were seeded onto poly-D-lysine coated 96-well-plates (100000 cells/well) the day before performing the FLIPR assay. The density of the cells in the 96-well-plate at the day of the FLIPR assay should be 90%. After aspiration of the culture media, BV-2 cells were incubated for 30 minutes at 37° C. with loading buffer and recovered in 150 µl HBSS buffer for 30 minutes at 37° C. After this procedure cells were stimulated with LPA (in HBSS pH 7.4 and 0.1% BSA) to determine the $EC_{50}$ of LPA in BV-2 cells. For the determination of the inhibitory effect of compounds of the formula I, test compounds were added to the cells in the 96-well-plate 10 minutes prior the addition of LPA. The $IC_{50}$ data of the above described FLIPR assay using the murine microglia cell line BV-2 for exemplary compounds of the present invention are shown in Table 3.

TABLE 2

| Example | $IC_{50}$ (μM) |
|---|---|
| 1 | 3.2 |
| 2 | 3.4 |
| 7 | 4.4 |
| 18 | 1.5 |
| 22 | 2.6 |
| 26 | 3.4 |
| 31 | 5.2 |
| 32 | 3.5 |
| 33 | 3.3 |
| 35 | 3.8 |
| 37 | 3.6 |
| 43 | 3.3 |
| 45 | 3.1 |
| 46 | 3.2 |
| 49 | 3.6 |
| 50 | 2.5 |
| 55 | 2.4 |
| 60 | 3.6 |
| 61 | 3.2 |
| 63 | 7.7 |

TABLE 3

| Example | $IC_{50}$ (μM) |
|---|---|
| 1 | 4.1 |
| 12 | 8.0 |
| 18 | 1.5 |

The invention claimed is:

1. A compound of the formula I,

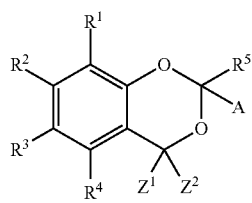

I wherein
A is selected from $R^{11}$—O—C(O)—, $R^{12}$—N($R^{13}$)—C(O)— and $Het^1$;
$R^1$, $R^2$, $R^3$ and $R^4$ are independently selected from hydrogen, halogen, $(C_1-C_4)$-alkyl, Ar—$(C_1-C_4)$-alkyl-, Ar, $Het^2$, $(C_1-C_4)$-alkyl-C(O)—, Ar—C(O)—, cyano, $R^{14}$—N($R^{15}$)—C(O)—, $Het^3$-C(O)—, hydroxy, $(C_1-C_4)$-alkyl-O—, Ar—O—, Ar—$(C_1-C_4)$-alkyl-O—, $(C_1-C_4)$-alkyl-S(O)$_n$—, Ar—S(O)$_n$—, $R^{11}$—N($R^{12}$)—S(O)$_2$—, $Het^3$-S(O)$_2$—, $(C_1-C_4)$-alkyl-NH—, di(($C_1-C_4)$-alkyl)N—, Ar—NH— and Ar—N(($C_1-C_4)$-alkyl)-, and either $R^1$ and $R^2$, or $R^2$ and $R^3$, or $R^3$ and $R^4$, together with the carbon atoms carrying them, can form a carbocyclic ring selected from benzene and 5-membered to 7-membered cycloalkane, wherein the benzene ring is unsubstituted or substituted by one or more substituents independently selected from halogen, $(C_1-C_4)$-alkyl, cyano, $(C_1-C_4)$-alkyl-O— and $(C_1-C_4)$-alkyl-S(O)$_n$—, and the cycloalkane ring is unsubstituted or substituted by one or more substituents independently selected from fluorine and $(C_1-C_4)$-alkyl;
$R^5$ is selected from hydrogen and $(C_1-C_4)$-alkyl;
$R^{11}$, $R^{12}$, $R^{13}$, $R^{14}$ and $R^{15}$ are independently selected from hydrogen and $(C_1-C_4)$-alkyl;
one of the groups $Z^1$ and $Z^2$ is $(C_3-C_8)$-cycloalkyl and the other is selected from hydrogen, $(C_1-C_8)$-alkyl, $(C_3-C_8)$-cycloalkyl and phenyl, wherein all cycloalkyl groups are independently unsubstituted or substituted by one or more substituents independently selected from fluorine, $(C_1-C_4)$-alkyl and $(C_1-C_4)$-alkyl-O—, and the phenyl group is unsubstituted or substituted by one or more substituents independently selected from halogen, $(C_1-C_4)$-alkyl, cyano, $(C_1-C_4)$-alkyl-O— and $(C_1-C_4)$-alkyl-S(O)$_n$—;
Ar is phenyl or an aromatic, 5-membered or 6-membered, monocyclic heterocycle which comprises one or two ring heteroatoms independently selected from N, O and S, which are all unsubstituted or substituted by one or more substituents independently selected from halogen, $(C_1-C_4)$-alkyl, cyano, $(C_1-C_4)$-alkyl-O— and $(C_1-C_4)$-alkyl-S(O)$_n$—;
$Het^1$ is a partially unsaturated or aromatic, 5-membered or 6-membered, monocyclic heterocycle which comprises one to four ring heteroatoms independently selected from N, O and S, bonded via a ring carbon atom, and unsubstituted or substituted by one or more substituents independently selected from $(C_1-C_4)$-alkyl, hydroxy and oxo;
$Het^2$ is a saturated, 4-membered to 7-membered, monocyclic heterocycle which comprises one or two ring heteroatoms independently selected from N, O and S, bonded via a ring carbon atom or a ring nitrogen atom, and unsubstituted or substituted by one or more substituents independently selected from fluorine and $(C_1-C_4)$-alkyl;
$Het^3$ is a saturated 4-membered to 7-membered, monocyclic heterocycle which comprises a ring nitrogen atom via which $Het^3$ is bonded, and zero or one further ring heteroatom selected from N, O and S, and unsubstituted or substituted by one or more substituents independently selected from fluorine and $(C_1-C_4)$-alkyl;
n is selected from the numbers 0, 1 and 2;
wherein
all alkyl groups are unsubstituted or substituted by one or more fluorine substituents;
in any of its stereoisomeric forms or a mixture of stereoisomeric forms in any ratio, or a pharmaceutically acceptable salt thereof;
provided that the compound of the formula I is not
6-chloro-4-cyclohexyl-4-phenyl-4H-benzo[1,3]dioxine-2-carboxylic acid,
6-chloro-4-cyclohexyl-4-phenyl-4H-benzo[1,3]dioxine-2-carboxylic acid methyl ester, or
6-chloro-4,4-dicyclohexyl-4H-benzo[1,3]dioxine-2-carboxylic acid.

2. A compound of the formula I according to claim 1, wherein
A is selected from $R^{11}$—O—C(O)—, $R^{12}$—N($R^{13}$)—C(O)— and $Het^1$;
$R^1$, $R^2$, $R^3$ and $R^4$ are independently selected from hydrogen, halogen, $(C_1-C_4)$-alkyl, Ar—$(C_1-C_4)$-alkyl-, Ar, $Het^2$, $(C_1-C_4)$-alkyl-C(O)—, Ar—C(O)—, $R^{14}$—N ($R^{15}$)—C(O)—, Het³-C(O)—, ($C_1$-$C_4$)-alkyl-O—, Ar—O—, Ar—($C_1$-$C_4$)-alkyl-O—, ($C_1$-$C_4$)-alkyl-S(O)$_n$—, Ar—S(O)$_n$—, $R^{11}$—N($R^{12}$)—S(O)$_2$—, Het³-S(O)$_2$—, ($C_1$-$C_4$)-alkyl-NH— and di(($C_1$-$C_4$)-alkyl)N—, and either $R^1$ and $R^2$, or $R^2$ and $R^3$, or $R^3$ and $R^4$, together with the carbon atoms carrying them, can form a carbocyclic ring selected from benzene and 5-membered or 6-membered cycloalkane, wherein the benzene ring is unsubstituted or substituted by one or more substituents independently selected from halogen and ($C_1$-$C_4$)-alkyl, and the cycloalkane ring is unsubstituted or substituted by one or more substituents independently selected from fluorine and ($C_1$-$C_4$)-alkyl;

$R^5$ is selected from hydrogen and ($C_1$-$C_4$)-alkyl;

$R^{11}$, $R^{12}$, $R^{13}$, $R^{14}$ and $R^{15}$ are independently selected from hydrogen and ($C_1$-$C_4$)-alkyl;

one of the groups $Z^1$ and $Z^2$ is ($C_3$-$C_8$)-cycloalkyl and the other is selected from hydrogen, ($C_1$-$C_8$)-alkyl, ($C_3$-$C_8$)-cycloalkyl and phenyl, wherein all cycloalkyl groups are independently unsubstituted or substituted by one or more substituents independently selected from fluorine, ($C_1$-$C_4$)-alkyl and ($C_1$-$C_4$)-alkyl-O—, and the phenyl group is unsubstituted or substituted by one or more substituents independently selected from halogen, ($C_1$-$C_4$)-alkyl, cyano, ($C_1$-$C_4$)-alkyl-O— and ($C_1$-$C_4$)-alkyl-S(O)$_n$—;

Ar is phenyl or an aromatic, 5-membered or 6-membered, monocyclic heterocycle which comprises one or two ring heteroatoms independently selected from N, O and S, which are all unsubstituted or substituted by one or more substituents independently selected from halogen, ($C_1$-$C_4$)-alkyl, cyano, ($C_1$-$C_4$)-alkyl-O— and ($C_1$-$C_4$)-alkyl-S(O)$_n$—;

Het¹ is a partially unsaturated or aromatic, 5-membered monocyclic heterocycle which comprises one to four ring heteroatoms independently selected from N, O and S, bonded via a ring carbon atom, and unsubstituted or substituted by one or more substituents independently selected from ($C_1$-$C_4$)-alkyl, hydroxy and oxo;

Het² is a saturated, 4-membered to 7-membered, monocyclic heterocycle which comprises one or two ring heteroatoms independently selected from N, O and S, bonded via a ring carbon atom or a ring nitrogen atom, and unsubstituted or substituted by one or more substituents independently selected from fluorine and ($C_1$-$C_4$)-alkyl;

Het³ is a saturated 4-membered to 7-membered, monocyclic heterocycle which comprises a ring nitrogen atom via which Het³ is bonded, and zero or one further ring heteroatom selected from N, O and S, and unsubstituted or substituted by one or more substituents independently selected from fluorine and ($C_1$-$C_4$)-alkyl;

n is selected from the numbers 0, 1 and 2;

wherein all alkyl groups are unsubstituted or substituted by one or more fluorine substituents;

in any of its stereoisomeric forms or a mixture of stereoisomeric forms in any ratio, or a pharmaceutically acceptable salt thereof.

3. A compound of the formula I according to claim 1, wherein

A is selected from $R^{11}$—O—C(O)— or Het¹;

$R^1$, $R^2$, $R^3$ and $R^4$ are independently selected from hydrogen, halogen, ($C_1$-$C_4$)-alkyl, Ar—($C_1$-$C_4$)-alkyl-, Ar, Het², ($C_1$-$C_4$)-alkyl-C(O)—, Ar—C(O)—, $R^{14}$—N($R^{15}$)—C(O)—, Het³-C(O)—, ($C_1$-$C_4$)-alkyl-O—, Ar—O—, Ar—($C_1$-$C_4$)-alkyl-O—, ($R^{11}$—N($R^{12}$)—S(O)$_2$—, Het³-S(O)$_2$—, ($C_1$-$C_4$)-alkyl-NH— and di(($C_1$-$C_4$)-alkyl)N—, and either $R^1$ and $R^2$, or $R^2$ and $R^3$, or $R^3$ and $R^4$, together with the carbon atoms carrying them, can form a carbocyclic ring selected from benzene and 5-membered or 6-membered cycloalkane, wherein the benzene ring is unsubstituted or substituted by one or more substituents independently selected from halogen and ($C_1$-$C_4$)-alkyl, and the cycloalkane ring is unsubstituted or substituted by one or more substituents independently selected from fluorine and ($C_1$-$C_4$)-alkyl;

$R^5$ is selected from hydrogen and ($C_1$-$C_4$)-alkyl;

$R^{11}$, $R^{12}$, $R^{14}$ and $R^{15}$ are independently selected from hydrogen and ($C_1$-$C_4$)-alkyl;

one of the groups $Z^1$ and $Z^2$ is ($C_3$-$C_8$)-cycloalkyl and the other is selected from hydrogen, ($C_1$-$C_4$)-alkyl, ($C_3$-$C_8$)-cycloalkyl and phenyl, wherein all cycloalkyl groups are independently unsubstituted or substituted by one or more substituents independently selected from fluorine and ($C_1$-$C_4$)-alkyl, and the phenyl group is unsubstituted or substituted by one or more substituents independently selected from halogen and ($C_1$-$C_4$)-alkyl;

Ar is phenyl or an aromatic, 5-membered or 6-membered, monocyclic heterocycle which comprises one or two ring heteroatoms independently selected from N, O and S, which are all unsubstituted or substituted by one or more substituents independently selected from halogen, ($C_1$-$C_4$)-alkyl and ($C_1$-$C_4$)-alkyl-O—;

Het¹ is selected from

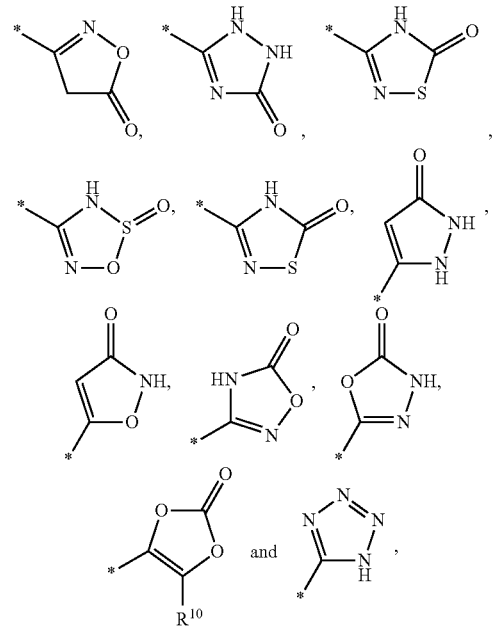

wherein $R^{10}$ is selected from hydrogen and ($C_1$-$C_4$)-alkyl;

Het² is a saturated, 5-membered or 6-membered, monocyclic heterocycle which comprises one or two ring heteroatoms independently selected from N, O and S, bonded via a ring carbon atom or a ring nitrogen atom, and unsubstituted or substituted by one or more substituents independently selected from fluorine and ($C_1$-$C_4$)-alkyl;

Het³ is a saturated 5-membered or 6-membered, monocyclic heterocycle which comprises a ring nitrogen atom via which Het³ is bonded, and zero or one further ring heteroatom selected from N, O and S, and unsubstituted or substituted by one or more substituents independently selected from fluorine and (C₁-C₄)-alkyl;
wherein
all alkyl groups are unsubstituted or substituted by one or more fluorine substituents;
in any of its stereoisomeric forms or a mixture of stereoisomeric forms in any ratio, or a pharmaceutically acceptable salt thereof.

4. A compound of the formula I according to claim 1, wherein
A is selected from R¹¹—O—C(O)—,

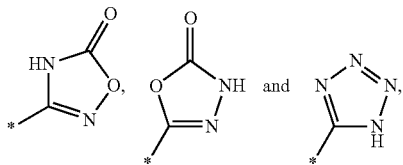

R¹, R², R³ and R⁴ are independently selected from hydrogen, halogen, (C₁-C₄)-alkyl, (C₁-C₄)-perfluoroalkyl, (C₁-C₄)-alkyl-O—, (C₁-C₄)-perfluoroalkyl-O—, phenyl, pyrrolyl, pyridinyl, pyridinyl-O—, pyrrolidinyl-S (O)₂—, morpholinyl, Ar—C(O)—, Ar—O—, di((C₁-C₄)-alkyl)N—, Ar—(C₁-C₄)-alkyl- and Ar—(C₁-C₄)-alkyl-O—,
and either the groups R¹ and R², or R² and R³, or R³ and R⁴, together with the carbon atoms carrying them, can form a benzene ring or a cyclohexane ring, wherein the benzene ring is unsubstituted or substituted by one or more substituents independently selected from halogen and (C₁-C₄)-alkyl, and the cyclohexane ring is unsubstituted or substituted by one or more substituents independently selected from fluorine and (C₁-C₄)-alkyl;
R⁵ is hydrogen or methyl;
Z¹ and Z² are identical and are (C₃-C₈)-cycloalkyl,
or one of the residues Z¹ and Z² is (C₃-C₈)-cycloalkyl and the other is hydrogen or phenyl;
Ar is phenyl unsubstituted or substituted by one or two substituents independently selected from halogen and (C₁-C₄)-alkyl-O—;
in any of its stereoisomeric forms or a mixture of stereoisomeric forms in any ratio, or a pharmaceutically acceptable salt thereof.

5. A compound of the formula I according to claim 1, selected from
4,4-Dicyclohexyl-7-pyrrol-1-yl-4H-benzo[1,3]dioxine-2-carboxylic acid,
4,4-Dicyclohexyl-6-methyl-4H-benzo[1,3]dioxine-2-carboxylic acid,
4,4-Dicyclohexyl-7-methoxy-4H-benzo[1,3]dioxine-2-carboxylic acid,
4,4-Dicyclohexyl-6-fluoro-4H-benzo[1,3]dioxine-2-carboxylic acid,
4,4-Dicyclohexyl-7-dimethylamino-4H-benzo[1,3]dioxine-2-carboxylic acid,
4,4-Dicyclohexyl-5,7-dimethoxy-4H-benzo[1,3]dioxine-2-carboxylic acid,
4,4-Dicyclohexyl-4H-naphtho[2,3-d][1,3]dioxine-2-carboxylic acid,
4,4-Dicyclohexyl-7-methyl-4H-benzo[1,3]dioxine-2-carboxylic acid,
4,4-Dicyclohexyl-5-methyl-4H-benzo[1,3]dioxine-2-carboxylic acid,
7-Chloro-4,4-dicyclohexyl-4H-benzo[1,3]dioxine-2-carboxylic acid,
4,4-Dicyclohexyl-8-methyl-4H-benzo[1,3]dioxine-2-carboxylic acid,
4,4-Dicyclohexyl-8-fluoro-4H-benzo[1,3]dioxine-2-carboxylic acid,
6-tert-Butyl-4,4-dicyclohexyl-4H-benzo[1,3]dioxine-2-carboxylic acid,
4,4-Dicyclohexyl-6-iodo-4H-benzo[1,3]dioxine-2-carboxylic acid,
4,4-Dicyclohexyl-6-trifluoromethyl-4H-benzo[1,3]dioxine-2-carboxylic acid,
6-Chloro-4,4-dicyclohexyl-2-methyl-4H-benzo[1,3]dioxine-2-carboxylic acid,
4,4-Dicyclohexyl-6-trifluoromethoxy-4H-benzo[1,3]dioxine-2-carboxylic acid,
6-Chloro-4,4-dicyclohexyl-7-fluoro-4H-benzo[1,3]dioxine-2-carboxylic acid,
6-Chloro-4,4-dicyclohexyl-8-fluoro-4H-benzo[1,3]dioxine-2-carboxylic acid,
6-Chloro-4,4-dicyclohexyl-5-fluoro-4H-benzo[1,3]dioxine-2-carboxylic acid,
6-(4-Chloro-phenoxy)-4,4-dicyclohexyl-4H-benzo[1,3]dioxine-2-carboxylic acid,
4,4-Dicyclohexyl-6-pyridin-4-yl-4H-benzo[1,3]dioxine-2-carboxylic acid,
4,4-Dicyclohexyl-6-(3-methoxy-phenoxy)-4H-benzo[1,3]dioxine-2-carboxylic acid,
6-(3-Chloro-phenoxy)-4,4-dicyclohexyl-4H-benzo[1,3]dioxine-2-carboxylic acid,
6-(4-Chloro-benzoyl)-4,4-dicyclohexyl-4H-benzo[1,3]dioxine-2-carboxylic acid,
4,4-Dicyclohexyl-6-(pyridin-3-yloxy)-4H-benzo[1,3]dioxine-2-carboxylic acid,
4,4-Dicyclohexyl-4H-benzo[1,3]dioxine-2-carboxylic acid,
4,4-Dicyclohexyl-8-methoxy-4H-benzo[1,3]dioxine-2-carboxylic acid,
4,4-Dicyclohexyl-5-ethoxy-4H-benzo[1,3]dioxine-2-carboxylic acid,
7-Butoxy-4,4-dicyclohexyl-4H-benzo[1,3]dioxine-2-carboxylic acid,
6,8-Dichloro-4,4-dicyclohexyl-4H-benzo[1,3]dioxine-2-carboxylic acid,
1,1-Dicyclohexyl-1H-naphtho[2,1-d][1,3]dioxine-3-carboxylic acid,
4,4-Dicyclohexyl-6-methoxy-4H-benzo[1,3]dioxine-2-carboxylic acid,
4,4-Dicyclohexyl-6-phenyl-4H-benzo[1,3]dioxine-2-carboxylic acid,
4,4-Dicyclohexyl-7-methoxy-5-methyl-4H-benzo[1,3]dioxine-2-carboxylic acid,
7-Benzyloxy-4,4-dicyclohexyl-4H-benzo[1,3]dioxine-2-carboxylic acid,
6-Chloro-4,4-dicyclohexyl-7-methoxy-4H-benzo[1,3]dioxine-2-carboxylic acid,
4,4-Dicyclohexyl-6-(pyrrolidine-1-sulfonyl)-4H-benzo[1,3]dioxine-2-carboxylic acid,
4,4-Dicyclohexyl-7-morpholin-4-yl-4H-benzo[1,3]dioxine-2-carboxylic acid,
4,4-Dicyclohexyl-4H-naphtho[1,2-d][1,3]dioxine-2-carboxylic acid,
6-Chloro-4,4-dicyclohexyl-8-methyl-4H-benzo[1,3]dioxine-2-carboxylic acid, 6-Chloro-4,4-dicyclohexyl-7-methyl-4H-benzo[1,3]dioxine-2-carboxylic acid,
4,4-Dicyclohexyl-5,7-difluoro-4H-benzo[1,3]dioxine-2-carboxylic acid,
1,1-Dicyclohexyl-7,8,9,10-tetrahydro-1H-naphtho[2,1-d][1,3]dioxine-3-carboxylic acid,
4,4-Dicyclohexyl-8-trifluoromethoxy-4H-benzo[1,3]dioxine-2-carboxylic acid,
8-tert-Butyl-4,4-dicyclohexyl-4H-benzo[1,3]dioxine-2-carboxylic acid,
10-Benzyl-4,4-dicyclohexyl-4H-naphtho[2,3-d][1,3]dioxine-2-carboxylic acid,
4,4-Dicyclohexyl-7-diethylamino-4H-benzo[1,3]dioxine-2-carboxylic acid,
6-Bromo-4,4-dicyclohexyl-4H-benzo[1,3]dioxine-2-carboxylic acid,
6-Chloro-4,4-dicyclopentyl-4H-benzo[1,3]dioxine-2-carboxylic acid,
6-Chloro-4-cycloheptyl-4H-benzo[1,3]dioxine-2-carboxylic acid,
6-Bromo-4,4-dicyclohexyl-4H-benzo[1,3]dioxine-2-carboxylic acid,
6-Chloro-4,4-dicycloheptyl-4H-benzo[1,3]dioxine-2-carboxylic acid,
6-Chloro-4,4-dicyclooctyl-4H-benzo[1,3]dioxine-2-carboxylic acid,
6-Chloro-4,4-dicycloheptyl-7-methyl-4H-benzo[1,3]dioxine-2-carboxylic acid,
4,4-Dicycloheptyl-6-trifluoromethoxy-4H-benzo[1,3]dioxine-2-carboxylic acid,
6-Bromo-4,4-dicycloheptyl-4H-benzo[1,3]dioxine-2-carboxylic acid,
5-(6-Chloro-4,4-dicyclohexyl-4H-benzo[1,3]dioxin-2-yl)-1H-tetrazole,
3-(6-Chloro-4,4-dicyclohexyl-4H-benzo[1,3]dioxin-2-yl)-4H-[1,2,4]oxadiazol-5-one,
6-Chloro-4,4-dicyclohexyl-4H-benzo[1,3]dioxine-2-carboxylic acid methyl ester, and
5-(6-Chloro-4,4-dicyclohexyl-4H-benzo[1,3]dioxin-2-yl)-3H-[1,3,4]oxadiazol-2-one,
in any of its stereoisomeric forms or a mixture of stereoisomeric forms in any ratio, or a pharmaceutically acceptable salt thereof.

6. A pharmaceutical composition comprising a compound of the formula I according to claim 1, or a pharmaceutically acceptable salt thereof, and a pharmaceutically acceptable carrier.

7. A method for the treatment of a disease responsive to the inhibition of the LPA receptor LPAR5, or for the reduction or inhibition of platelet aggregation, thrombus formation, activation of mast cells, or activation of microglial cells in a patient in need thereof, the method comprising administering a compound of the formula I according to claim 1, or a pharmaceutically acceptable salt thereof.

8. A method for the treatment of thromboembolic diseases, deep vein thrombosis, venous or arterial thromboembolism, thrombophlebitis, coronary or cerebral arterial thrombosis, cerebral embolism, renal embolism, pulmonary embolism, disseminated intravascular coagulation, cardiovascular disorders, transient ischemic attacks, strokes, acute myocardial infarction, peripheral vascular disease, preeclampsia/eclampsia, thrombotic cytopenic purpura, inflammatory disorders, hyperalgesia, asthma, multiple sclerosis, inflammatory pain, angiogenesis, allergic responses, or restenosis in a patient in need thereof, the method comprising administering a compound of the formula I according to claim 1, or a pharmaceutically acceptable salt thereof.

9. A method for the treatment of abnormal thrombus formation, acute myocardial infarction, thromboembolism, acute vessel closure associated with thrombolytic therapy or percutaneous transluminal coronary angioplasty (PTCA), transient ischemic attacks, stroke, intermittent claudication, bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, a risk of pulmonary thromboembolism, or disseminated systemic intravascular coagulatopathy occurring in vascular systems during septic shock, viral infections or cancer in a patient in need thereof, the method comprising administering a compound of the formula I according to claim 1, or a pharmaceutically acceptable salt thereof.

10. A method for the treatment of inflammatory pain, asthma, angiogenesis, demyelating diseases of the central nervous system or the peripheral nervous system, multiple sclerosis, transverse myelitis, optic neuritis, Devic's disease, Guillain-Barre syndrome or chronic inflammatory demyelinating polyneuropathy in a patient in need thereof, the method comprising administering a compound of the formula I according to claim 1, or a pharmaceutically acceptable salt thereof.

* * * * *